(12) United States Patent
Hathaway et al.

(10) Patent No.: US 10,470,898 B2
(45) Date of Patent: Nov. 12, 2019

(54) ORTHOPAEDIC INSTRUMENT SYSTEM FOR SURGICALLY-PREPARING A PATIENT'S TIBIA

(71) Applicant: DePuy Ireland Unlimited Company, Ringaskiddy, County Cork (IE)

(72) Inventors: Tyler S. Hathaway, Auburn, IN (US); Adam Carver, Fort Wayne, IN (US); Thomas E. Wogoman, Warsaw, IN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 203 days.

(21) Appl. No.: 15/598,622

(22) Filed: May 18, 2017

(65) Prior Publication Data

US 2017/0333214 A1   Nov. 23, 2017

Related U.S. Application Data

(60) Provisional application No. 62/338,284, filed on May 18, 2016.

(51) Int. Cl.
*A61F 2/46* (2006.01)
*A61F 2/38* (2006.01)
(Continued)

(52) U.S. Cl.
CPC ............ *A61F 2/461* (2013.01); *A61B 17/157* (2013.01); *A61B 17/164* (2013.01); *A61B 17/1675* (2013.01); *A61F 2/385* (2013.01); *A61F 2/389* (2013.01); *A61F 2/3859* (2013.01); *A61F 2/4684* (2013.01); *A61B 17/1604* (2013.01); *A61B 17/1717* (2013.01); *A61B 17/1764* (2013.01); *A61B 2017/0046* (2013.01); *A61B 2090/036* (2016.02);
(Continued)

(58) Field of Classification Search
CPC .............................. A61F 2/389; A61B 17/157
See application file for complete search history.

(56) References Cited

U.S. PATENT DOCUMENTS 3,727,928 A * 4/1973 Benjamin ............. B23B 31/208
                                                        279/133
4,710,075 A   12/1987 Davison
(Continued)

FOREIGN PATENT DOCUMENTS

| CN | 101742972 A | 6/2010 |
| CN | 101849864 A | 10/2010 |

(Continued)

OTHER PUBLICATIONS

International Search Report, International Application No. PCT/US2017/033295, dated Sep. 4, 2017, 14 pages.
(Continued)

*Primary Examiner* — David W Bates
(74) *Attorney, Agent, or Firm* — Barnes & Thornburg LLP

(57) ABSTRACT

An orthopedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

11 Claims, 26 Drawing Sheets

(51) Int. Cl.
*A61B 17/15* (2006.01)
*A61B 17/16* (2006.01)
*A61B 17/17* (2006.01)
*A61B 17/00* (2006.01)
*A61F 2/30* (2006.01)
*A61B 90/00* (2016.01)

(52) U.S. Cl.
CPC ........... *A61F 2002/30405* (2013.01); *A61F 2002/30507* (2013.01); *A61F 2002/30512* (2013.01); *A61F 2002/30538* (2013.01); *A61F 2002/30555* (2013.01); *A61F 2002/30736* (2013.01); *A61F 2002/3863* (2013.01); *A61F 2002/4624* (2013.01); *A61F 2002/4662* (2013.01); *A61F 2002/4681* (2013.01); *A61F 2002/4687* (2013.01)

(56) References Cited

U.S. PATENT DOCUMENTS

| | | |
|---|---|---|
| 4,952,213 A | 8/1990 | Bowman et al. |
| 5,100,409 A | 3/1992 | Coates et al. |
| 5,176,684 A | 1/1993 | Ferrante et al. |
| 5,356,414 A | 10/1994 | Cohen et al. |
| 5,415,662 A | 5/1995 | Ferrante et al. |
| 5,569,259 A | 10/1996 | Ferrante et al. |
| 5,571,194 A | 11/1996 | Gabriel |
| 5,601,563 A | 2/1997 | Burke et al. |
| 5,613,970 A | 3/1997 | Houston et al. |
| 5,634,927 A | 6/1997 | Houston et al. |
| 5,681,316 A | 10/1997 | DeOrio et al. |
| 5,683,397 A | 11/1997 | Vendrely et al. |
| 5,702,460 A | 12/1997 | Carls et al. |
| 5,769,854 A | 6/1998 | Bastian et al. |
| 5,931,841 A | 8/1999 | Ralph |
| 5,976,147 A | 11/1999 | LaSalle et al. |
| 6,488,687 B1 | 12/2002 | Masini |
| 6,575,980 B1 | 6/2003 | Robie et al. |
| 6,945,145 B1* | 9/2005 | Kesinger ........... B23B 31/207 279/42 |
| 7,497,874 B1 | 3/2009 | Metzger et al. |
| 7,547,327 B2 | 6/2009 | Collazo |
| 7,744,600 B2 | 6/2010 | Rangaiah et al. |
| 7,963,968 B2 | 6/2011 | Dees, Jr. |
| 8,002,777 B2 | 8/2011 | Fox et al. |
| 8,038,681 B2 | 10/2011 | Koenemann |
| 8,187,280 B2 | 5/2012 | May et al. |
| 8,377,141 B2 | 2/2013 | McMinn |
| 8,425,524 B2 | 4/2013 | Aker et al. |
| 8,771,280 B2 | 7/2014 | Bailey et al. |
| 8,986,310 B2 | 3/2015 | Bailey et al. |
| 9,028,501 B2 | 5/2015 | Thomas et al. |
| 9,113,915 B2 | 8/2015 | Thomas et al. |
| 9,579,113 B2 | 2/2017 | Thomas et al. |
| 9,636,122 B2 | 5/2017 | Chaney et al. |
| 9,962,173 B2 | 5/2018 | Thomas et al. |
| 2001/0001121 A1 | 5/2001 | Lombardo et al. |
| 2003/0114859 A1 | 6/2003 | Grusin et al. |
| 2004/0039450 A1 | 2/2004 | Griner et al. |
| 2004/0078043 A1 | 4/2004 | Masini |
| 2004/0087960 A1 | 5/2004 | Kinnett |
| 2004/0153087 A1 | 8/2004 | Sanford et al. |
| 2004/0225368 A1 | 11/2004 | Plumet et al. |
| 2005/0192588 A1 | 9/2005 | Garcia |
| 2006/0173463 A1 | 8/2006 | Dees |
| 2006/0195113 A1 | 8/2006 | Masini |
| 2006/0241634 A1 | 10/2006 | Tuttle et al. |
| 2007/0010890 A1 | 1/2007 | Collazo |
| 2007/0073305 A1 | 3/2007 | Lionberger et al. |
| 2007/0173850 A1 | 7/2007 | Rangaiah et al. |
| 2008/0091273 A1 | 4/2008 | Hazebrouck |
| 2008/0183177 A1 | 7/2008 | Fox et al. |
| 2008/0228189 A1 | 9/2008 | Fox et al. |
| 2008/0312659 A1 | 12/2008 | Metzger et al. |
| 2009/0088762 A1 | 4/2009 | Koenemann |
| 2009/0088763 A1 | 4/2009 | Aram et al. |
| 2009/0125114 A1 | 5/2009 | May et al. |
| 2009/0204115 A1 | 8/2009 | Dees, Jr. et al. |
| 2009/0222008 A1 | 9/2009 | Hogg et al. |
| 2010/0076441 A1 | 3/2010 | May et al. |
| 2010/0121334 A1 | 5/2010 | Couture et al. |
| 2010/0234850 A1* | 9/2010 | Dees, Jr. ........... A61B 17/155 606/87 |
| 2011/0093081 A1 | 4/2011 | Chana et al. |
| 2011/0218541 A1 | 9/2011 | Bailey et al. |
| 2011/0307067 A1 | 12/2011 | Dees |
| 2012/0310246 A1 | 12/2012 | Belcher et al. |
| 2012/0323334 A1 | 12/2012 | Jones et al. |
| 2013/0144296 A1 | 6/2013 | Yoko et al. |
| 2013/0165936 A1 | 6/2013 | Myers |
| 2013/0325014 A1 | 12/2013 | Sordelet et al. |
| 2013/0325016 A1 | 12/2013 | Sordelet et al. |
| 2013/0325018 A1 | 12/2013 | Thomas et al. |
| 2013/0325019 A1 | 12/2013 | Thomas et al. |
| 2013/0325021 A1 | 12/2013 | Sordelet et al. |
| 2013/0325136 A1 | 12/2013 | Thomas et al. |
| 2014/0276858 A1 | 9/2014 | Major et al. |
| 2016/0089161 A1 | 3/2016 | Ardito et al. |

FOREIGN PATENT DOCUMENTS

| | | |
|---|---|---|
| CN | 101879099 A | 11/2010 |
| EP | 0947169 A2 | 10/1999 |
| EP | 2145590 A1 | 1/2010 |
| EP | 2777550 A2 | 9/2014 |
| EP | 2777556 A2 | 9/2014 |
| FR | 2748389 A1 | 11/1997 |
| FR | 2752519 A1 | 2/1998 |
| FR | 2943528 A1 | 10/2010 |
| GB | 2323037 A | 9/1998 |
| JP | 11104155 A | 4/1999 |
| JP | 2009006066 A | 1/2009 |
| JP | 2010057527 A | 3/2010 |
| WO | 9625123 A2 | 8/1996 |
| WO | 9730661 A1 | 8/1997 |
| WO | 9852499 A1 | 11/1998 |
| WO | 0013597 A1 | 3/2000 |
| WO | 2007041644 A1 | 4/2007 |
| WO | 2007114841 A1 | 10/2007 |
| WO | 2010019284 A1 | 2/2010 |

OTHER PUBLICATIONS

Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
Redacted Memorandum with Appendix A, dated Jan. 26, 2010, outlining a surgical instrument evaluation that commmenced in 2010, 37 pages.
"Reinstall Wave 1 Evaluation Surgical Technique," used during the surgical instrument evaluation that commenced in 2010, 36 pages.

(56) References Cited

OTHER PUBLICATIONS

Tray configuration cards showing the instruments used during the surgical instrument evaluation that commenced in 2010, 8 pages.
International Search Report and Written Opinion, International Application No. PCT/US2017/033295, dated Dec. 18, 2017, 8 pages.
International Search Report issued in connection with International Application No. PCT/US2017/033307, dated Sep. 25, 2017, 13 pages.
International Search Report and Written Opinion, International Application No. PCT/US2017/033278, dated Nov. 21, 2017, 8 pages.

* cited by examiner

ORTHOPAEDIC INSTRUMENT SYSTEM FOR SURGICALLY-PREPARING A PATIENT'S TIBIA The present application claims priority under 35 U.S.C. § 119 to U.S. Patent Application Ser. No. 62/338,284, filed May 18, 2016, and having the title "SYSTEM AND METHOD FOR PREPARING A PATIENT'S TIBIA IN AN ORTHOPAEDIC JOINT REPLACEMENT PROCEDURE," which is herein incorporated by reference in its entirety.

CROSS-REFERENCE TO RELATED APPLICATIONS

Cross reference is made to U.S. Patent Application Ser. No. 62/338,276 entitled "SYSTEM AND METHOD FOR PREPARING A PATIENT'S FEMUR IN AN ORTHOPAEDIC JOINT REPLACEMENT PROCEDURE;" and U.S. Patent Application Ser. No. 62/338,468 entitled "SYSTEM AND METHOD FOR PREPARING A PATIENT'S BONE TO RECEIVE A PROSTHETIC COMPONENT," each of which is assigned to the same assignee as the present application, each of which is filed concurrently herewith, and each of which is hereby incorporated by reference.

Cross reference is made to copending U.S. patent application Ser. No. 15/598,624 entitled "SYSTEM FOR PREPARING A PATIENT'S TIBIA IN AN ORTHOPAEDIC JOINT REPLACEMENT PROCEDURE"; and copending U.S. patent application Ser. No. 15/598,626 entitled "METHOD FOR PREPARING A PATIENT'S TIBIA IN AN ORTHOPAEDIC JOINT REPLACEMENT PROCEDURE", each of which is assigned to the same assignee as the present application, each of which is filed concurrently herewith, and each of which is hereby incorporated by reference.

TECHNICAL FIELD

The present disclosure relates generally to an orthopaedic prosthesis system, including prosthetic components and instruments for use in the performance of an orthopaedic joint replacement procedure, and more particularly to orthopaedic prosthetic components and surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

From time-to-time, a revision knee surgery may need to be performed on a patient. In such a revision knee surgery, the previously-implanted knee prosthesis, sometimes referred to a "primary knee prosthesis," is surgically removed and a replacement or revision knee prosthesis is implanted. In some revision knee surgeries, all of the components of the primary knee prosthesis, including, for example, the tibial tray, the femoral component, and the polymer bearing, may be surgically removed and replaced with revision prosthetic components. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

An orthopaedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

According to one aspect of the disclosure, an orthopaedic surgical instrument system includes a surgical reamer including an elongated shaft and a plurality of cutting flutes defined at a distal end of the elongated shaft. An attachment base includes a housing including a main body, an elongated bore that is sized to receive the elongated shaft of the reamer and extends along a longitudinal axis of the main body, and a rail extending from the main body orthogonal to the longitudinal axis. A locking knob is secured to the housing and has a longitudinal bore aligned with the elongated bore of the housing that is sized to receive the elongated shaft of the reamer. The locking knob is rotatable between a first position in which the attachment base is permitted to slide along the elongated shaft of the surgical reamer and a second position in which the attachment base is locked into position on the elongated shaft of the surgical reamer. A mounting frame is positioned on the rail. The mounting frame is configured to slide relative to the housing along the rail. A cutting block is removably coupled to the mounting frame. The locking knob is operable to advance a section of the housing into engagement with the reamer when rotated to the second position.

In some embodiments, the housing of the attachment base may have a retaining flange configured to engage an inner rib of the locking knob to secure the locking knob to the housing. In some embodiments, the housing of the attachment base may have an upper shaft extending outwardly from the main body along the longitudinal axis. The upper shaft may have a plurality of outer threads and the retaining flange. The locking knob may have a plurality of inner threads configured to engage the plurality of outer threads of the upper shaft. In some embodiments, the locking knob may be moveable along the longitudinal axis between an engaged position in which the plurality of inner threads are engaged with the plurality of outer threads of the upper shaft and a disengaged position in which the plurality of inner threads are spaced apart from the plurality of outer threads of the upper shaft. In some embodiments, the upper shaft may have a plurality of beams that extend along the longitudinal axis. Each beam may be spaced apart from an adjacent beam by an elongated slot. The retaining flange may have a plurality of retaining flanges. Each retaining flange may extend from a tip of each beam. In some embodiments, each beam may have a ramped upper surface. The locking knob may have an annular rib having a conical lower surface that may be configured to engage the ramped upper surface of each beam to advance the beams into engagement with the elongated shaft of the surgical reamer.

In some embodiments, the mounting frame may have a locking mechanism that may be operable to selectively secure the mounting frame in a position along the rail. In some embodiments, the mounting frame may have a second locking mechanism that may be operable to removeably couple the cutting block to the mounting frame.

In some embodiments, the rail may have a planar outer surface. The mounting frame may have a planar inner surface that corresponds to and engages the planar outer surface of the rail to prevent the mounting frame from rotating about the rail. In some embodiments, the cutting block may have a plurality of cutting guides sized for insertion of a cutting tool during resection of the patient's tibia. In some embodiments, an alignment guide plate may be sized to be received in one of a plurality of cutting guides of the cutting block to assess a resection of the patient's tibia.

According to another aspect of the disclosure, an orthopaedic surgical instrument system includes a housing including a main body, an elongated bore that is sized to receive an elongated shaft of a surgical reamer and that extends along a longitudinal axis of the main body, and a rail extending from the main body orthogonal to the longitudinal axis. A locking knob is secured to the housing and has a bore aligned with the elongated bore of the housing that is sized to receive the elongated shaft of the reamer. The locking knob is rotatable between a first position in which the elongated bore of the housing includes an opening having a first diameter and a second position in which the opening of the elongated bore has a second diameter that is less than the first diameter to lock the housing into position on the elongated shaft of the surgical reamer.

In some embodiments, the housing may have an upper shaft extending outwardly from the main body along the longitudinal axis. The upper shaft may have a plurality of outer threads and define the opening. The locking knob may have a plurality of inner threads configured to engage the plurality of outer threads of the upper shaft. In some embodiments, the locking knob may be moveable along the longitudinal axis between an engaged position in which the plurality of inner threads are engaged with the plurality of outer threads of the upper shaft and a disengaged position in which the plurality of inner threads are spaced apart from the plurality of outer threads of the upper shaft. In some embodiments, the upper shaft may have a plurality of beams that extend along the longitudinal axis. Each beam may be spaced apart from an adjacent beam by an elongated slot and may have a ramped upper surface. The locking knob may have an annular rib having a conical lower surface that may be configured to engage the ramped upper surface to cause the beams to decrease the opening from the first diameter to the second diameter.

In some embodiments, a mounting frame may be positioned on the rail. The mounting frame may be configured to slide relative to the housing along the rail and may have a bracket sized to receive a cutting block. In some embodiments, the mounting frame may have a locking mechanism that may be operable to selectively secure the mounting frame in a position along the rail. In some embodiments, a cutting block may be removably coupled to the mounting frame.

In some embodiments, the rail may have a planar outer surface. The mounting frame may have a planar inner surface that corresponds to and engages the planar outer surface of the rail to prevent the mounting frame from rotating about the rail.

According to yet another aspect of the disclosure, an orthopaedic surgical instrument system includes a first surgical reamer including an elongated shaft and a plurality of cutting flutes defined at a distal end of the elongated shaft. A tibial base plate includes a central opening extending along a first longitudinal axis and a pair of fixation bores. An offset guide includes an upper drum, a lower plate sized to be positioned in the central opening of the tibial base plate, and a bore extending through the offset guide along a second longitudinal axis that is offset from the first longitudinal axis of the tibial base plate when the offset guide is positioned on the tibial base plate. The bore is sized to receive the elongated shaft of the surgical reamer. A reamer guide body has a passageway defined therein that is configured to be substantially aligned with the central opening of the tibial base plate when the reamer guide body is positioned on the tibial base plate. The reamer guide body also includes a pair of fixation pins. Each of the fixation pins extends downwardly from the bottom surface of the guide body and is sized to be received in and extend outwardly from each of the fixation bores of the tibial base plate when the guide body is positioned on the tibial base plate. The offset guide is operable to rotate such that the lower plate of the offset guide engages the tibial base plate to rotate the tibial base plate about the second longitudinal axis.

In some embodiments, the offset guide may have a conical inner surface that defines the bore. The conical inner surface may extend from an upper opening to a lower opening smaller than the upper opening. In some embodiments, the offset guide may have a plurality of offset guides. Each offset guide may have a second longitudinal axis offset from the first longitudinal axis of the tibial base plate by a distance different from the offsets of the other offset guides. In some embodiments, the distance of one offset guide may be equal to zero millimeters.

In some embodiments, a second surgical reamer may be sized to extend through the passageway of the reamer guide body. The second surgical reamer may have an elongated shaft and a plurality of cutting flutes defined at a distal end. The plurality of cutting flutes may define a distal frustoconical cutting section, a proximal cutting section having a first diameter, and a cylindrical middle cutting section having a second diameter smaller than the first diameter.

In some embodiments, a second tibial base plate may have a central opening and a pair of slots extending outwardly from the central opening. A punch instrument may have a pair of arms sized to be positioned in the pair of slots of the second tibial base plate. Each arm may have a plurality of cutting teeth. In some embodiments, an impaction handle may have a locking flange configured to pivot between a locked position and an unlocked position. The punch instrument may have a plate configured to engage the locking flange when the locking flange is in the locked position. In some embodiments, the impaction handle may have a proximal post extending along a longitudinal axis. The impaction handle may have a bracket coupled to the proximal post and operable to move along the longitudinal axis relative to the post. The bracket may have an elongated slot defined therein. The impaction handle may have a lever arm that may be pivotally coupled to the proximal post. The lever arm may have the locking flange and a tab positioned in the elongated slot defined in the bracket. When the bracket is moved in a distal direction along the longitudinal axis, the tab may be advanced along the elongated slot and the lever arm may be pivoted from the locked position to the unlocked position. In some embodiments, a biasing element may be operable to bias the lever arm in the locked position.

In some embodiments, an attachment device may be configured to be secured to the elongated shaft of the first surgical reamer. A tibial cutting block may be configured to be coupled to the attachment device.

According to an aspect of the disclosure, an orthopaedic surgical instrument system includes a first surgical reamer including an elongated shaft and a plurality of cutting flutes defined at a distal end of the elongated shaft. A tibial base plate includes a central opening extending along a first longitudinal axis and a pair of fixation bores. An offset guide includes an upper drum, a lower plate sized to be positioned in the central opening of the tibial base plate, and a bore extending through the offset guide along a second longitudinal axis that is offset from the first longitudinal axis of the tibial base plate when the offset guide is positioned on the tibial base plate. The bore is sized to receive the elongated shaft of the surgical reamer. An attachment device is configured to be secured to the elongated shaft of the first surgical reamer. The attachment device includes a locking knob sized receive the elongated shaft of the first surgical reamer. A tibial cutting block is configured to be coupled to the attachment device. The tibial cutting block includes a cutting slot sized to receive a cutting tool to surgically-prepare a patient's tibia to receive the tibial base plate. The locking knob may be operable to advance a section of the attachment device into engagement with the first surgical reamer to lock the attachment device position on the elongated shaft of the first surgical reamer.

In some embodiments, a second tibial base plate may have a central opening and a pair of slots extending outwardly from the central opening. A punch instrument may have a pair of arms sized to be positioned in the pair of slots of the second tibial base plate. Each arm may have a plurality of cutting teeth.

In some embodiments, an impaction handle may have a locking flange configured to pivot between a locked position and an unlocked position. The punch instrument may have a plate configured to engage the locking flange when the locking flange is in the locked position. In some embodiments, the impaction handle may have a proximal post extending along a longitudinal axis. The impaction handle may have a bracket coupled to the proximal post and operable to move along the longitudinal axis relative to the post. The bracket may have an elongated slot defined therein. The impaction handle may have a lever arm that may be pivotally coupled to the proximal post. The lever arm may have the locking flange and a tab positioned in the elongated slot defined in the bracket. When the bracket is moved in a distal direction along the longitudinal axis, the tab may be advanced along the elongated slot and the lever arm may be pivoted from the locked position to the unlocked position. In some embodiments, a biasing element may be operable to bias the lever arm in the locked position.

In some embodiments, a reamer guide body may have a passageway defined therein that may be configured to be substantially aligned with the central opening of the tibial base plate when the reamer guide body is positioned on the tibial base plate. In some embodiments, a second surgical reamer may be sized to extend through the passageway of the reamer guide body. The second surgical reamer may have an elongated shaft and a plurality of cutting flutes defined at a distal end. The plurality of cutting flutes may define a distal frustoconical cutting section, a proximal cutting section having a first diameter, and a cylindrical middle cutting section having a second diameter smaller than the first diameter.

According to another aspect of the disclosure, a method of preparing a patient's tibia for a tibial prosthetic component includes inserting a surgical reamer into a cavity formed in a proximal end of a patient's tibia. The method also includes coupling an attachment device to an elongated shaft of the reamer such that the elongated shaft extends through a bore of a locking knob and a bore of a housing of the attachment device. The method also includes rotating the locking knob about the elongated shaft such that to compress a section of the housing engages the elongated shaft of the reamer. The method also includes coupling a mounting frame to a rail extending from the housing at an orthogonal angle with respect to the longitudinal axis. The method also includes coupling a cutting block to the mounting frame. The method also includes advancing a saw blade through a cutting guide formed in the cutting block to cut the proximal end of the patient's tibia.

In some embodiments, rotating the locking knob may require advancing a bottom surface of the locking knob toward a shoulder surface of the housing. In some embodiments, rotating the locking knob may require advancing a plurality of beams of the housing into engagement with the elongated shaft of the surgical reamer. In some embodiments, rotating the locking knob may require advancing an annular rib of the locking knob into engagement with a ramped upper surface of each of the plurality of beams to advance the plurality of beams of the housing into engagement with the elongated shaft of the surgical reamer. In some embodiments, rotating the locking knob may require engaging a threaded inner surface of the locking knob with a threaded outer surface of each of the plurality of beams.

In some embodiments, rotating the locking knob may require gripping an angled outer surface of the locking knob. In some embodiments, the method may require operating a locking mechanism to selectively secure the mounting frame to the rail. In some embodiments, the method may require inserting the rail into a bore extending through the mounting frame such that the mounting frame moves longitudinally on the mounting post to position the cutting block relative the patient's tibia. In some embodiments, the method may require engaging a planar outer surface of the mounting post with a planar inner surface of the bore of the mounting frame to prevent the mounting frame from rotating about the mounting post.

In some embodiments, the method may require removing the attachment device, the mounting frame, and the cutting block from the patient's tibia. The method may require positioning a tibial base plate on the proximal end of the patient's tibia such that the elongated shaft of the surgical reamer extends through a central opening of the tibial base plate. The method may require advancing an end of the elongated shaft into a bore defined in an offset guide, wherein the bore extends along a longitudinal axis that may be spaced apart from a longitudinal axis of the central opening. The method may require positioning the offset guide within the central opening of the tibial plate. The method may require rotating the offset guide to rotate the tibial plate relative a proximal end of the patient's tibia. The method may require determining an offset orientation of a tibial prosthetic component based on the orientation of the tibial plate relative to the proximal end of the patient's tibia.

In some embodiments, the method may require removing the offset guide and the surgical reamer from the patient's tibia. The method may require positioning a reamer guide body on the tibial base plate. The method may require inserting a second surgical reamer into the reamer guide body. The second surgical reamer may have a plurality of cutting flutes that define (i) a distal frustoconical cutting section, (ii) a proximal cutting section having a first diameter, and (iii) a cylindrical middle cutting section having a second diameter smaller than the first diameter.

In some embodiments, the method may require advancing a drill stop along an elongated shaft of the second surgical reamer. In some embodiments, inserting the second surgical reamer into the reamer guide body may require advancing the second surgical reamer into the patient's tibia and using the drill stop to determine a maximum reaming depth.

In some embodiments, the method may require removing the offset guide from the surgical reamer, wherein the offset guide may be a first offset guide of a plurality of offset guides. The method may require selecting a second offset guide of the plurality of offset, wherein the second offset guide has a second bore. The method may require advancing an end of the elongated shaft into the second bore of the second offset guide, wherein the second bore extends along a second longitudinal axis that may be spaced apart from the longitudinal axis of the central opening by an amount different from longitudinal axis of the first offset guide. The method may require rotating the second offset guide to rotate the tibial plate relative a proximal end of the patient's tibia to determine the offset orientation.

According to yet another aspect of the disclosure, a method of preparing a patient's tibia for a tibial prosthetic component includes inserting a first surgical reamer into a cavity formed in a proximal end of a patient's tibia. The method also includes positioning a tibial base plate on the proximal end of the patient's tibia such that the elongated shaft of the first surgical reamer extends through a central opening of the tibial base plate. The method also includes advancing an end of the elongated shaft into a bore defined in an offset guide, wherein the bore extends along a longitudinal axis that may be spaced apart from a longitudinal axis of the central opening. The method also includes positioning the offset guide within the central opening of the tibial plate. The method also includes rotating the offset guide to rotate the tibial base plate relative a proximal end of the patient's tibia. The method also includes determining an offset orientation of a tibial prosthetic component based on the orientation of the tibial plate relative to the proximal end of the patient's tibia. The method also includes removing the offset guide and the first surgical reamer from the patient's tibia. The method also includes positioning a reamer guide body on the tibial base plate. The method also includes inserting a second surgical reamer into the reamer guide body, wherein the second surgical reamer includes a plurality of cutting flutes that define (i) a distal frustoconical cutting section, (ii) a proximal cutting section having a first diameter, and (iii) a cylindrical middle cutting section having a second diameter smaller than the first diameter.

In some embodiments, the method may require positioning a depth stop on the elongated shaft of the second surgical reamer. The depth stop may have a moveable flange sized to be separately received in an aperture defined in the elongated shaft of the second surgical reamer. The method may require actuating a user-operated button of the depth stop to engage the flange with the annular slot.

In some embodiments, the method may require removing the offset guide from the surgical reamer, wherein the offset guide may be a first offset guide of a plurality of offset guides. The method may require selecting a second offset guide of the plurality of offset, wherein the second offset guide has a second bore. The method may require advancing an end of the elongated shaft into the second bore of the second offset guide, wherein the second bore extends along a second longitudinal axis that may be spaced apart from the longitudinal axis of the central opening by an amount different from longitudinal axis of the first offset guide. The method may require rotating the second offset guide to rotate the tibial plate relative a proximal end of the patient's tibia to determine the offset orientation.

BRIEF DESCRIPTION OF THE DRAWINGS

The detailed description particularly refers to the following figures, in which:

FIGS. 22A-24 illustrate a number of steps of a surgical procedure utilizing the orthopaedic joint replacement system.

DETAILED DESCRIPTION OF THE DRAWINGS

Figure 1:
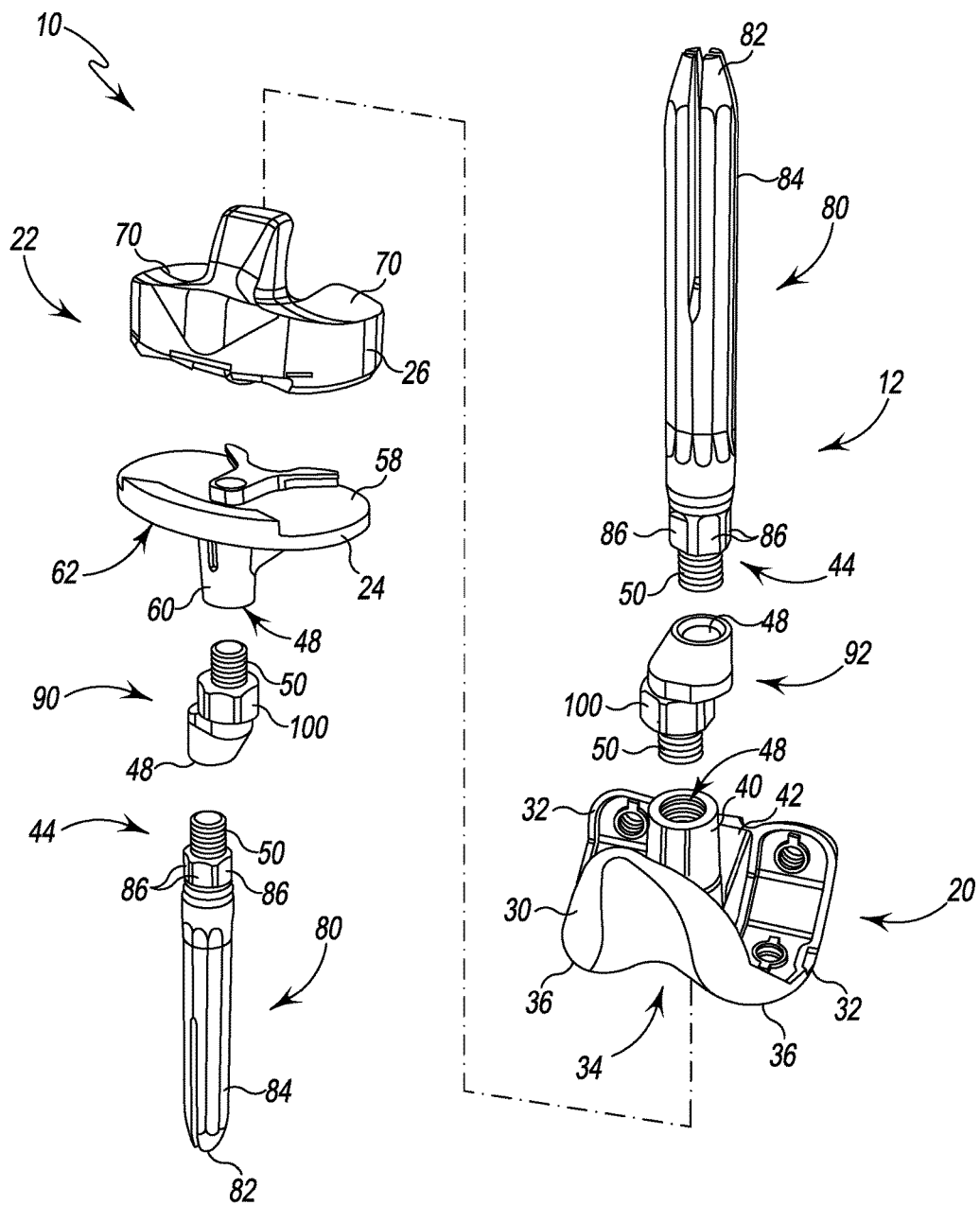
FIG. 1 is an exploded perspective view of prosthetic components of an orthopaedic joint replacement system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referring now to FIG. 1, the orthopaedic joint replacement system 10 includes a number of orthopaedic prosthetic components 12 and a number of orthopaedic surgical instruments 14 (see, for example, FIG. 2) for use in preparing the bone to receive one or more of the prosthetic components 12. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic prosthetic components or implants, such as those shown in FIG. 1.

The prosthetic components 12 of the system 10 include a prosthetic femoral component 20 configured to be secured to a surgically-prepared distal end of a patient's femur and a prosthetic tibial component 22 configured to be secured to a surgically-prepared proximal end of the patient's tibia. In the illustrative embodiment, the tibial component 22 includes a tibial tray 24 and a prosthetic insert 26 configured to engage the femoral component 20 after implantation into a patient's knee. It should be appreciated that the system 10 may include a number of components 12 corresponding to patients having bones of varying sizes. In that way, a surgeon will be able to select the components and other instruments that most-closely match the patient's bony anatomy.

As shown in FIG. 1, the femoral component 20 includes an anterior flange 30 and a pair of condyles 32 extending away from the flange 30. A notch 34, commonly called an intra-condylar notch, is defined between the condyles 32. The condyles 32 define articulation surfaces 36 configured to engage corresponding articulation surfaces 70 of the insert 26. The femoral component 20 also includes an elongated stem post 40, which extends superiorly away from its backside surface 42. As described in greater detail below, the femoral stem post 40 is configured to receive one of a number of different stem components 44. In the illustrative embodiment, a threaded bore 48, which is sized to receive a corresponding threaded shaft 50 of a stem component 44, is defined in the stem post 40.

The tibial tray 24 is configured to be implanted into a surgically-prepared end of a patient's proximal tibia (not shown). The tibial tray 24 includes a platform 58 having an elongated stem post 60 extending inferiorly away from its inferior surface 62. The elongated tibial stem post 60 is configured to receive one of a number of different stem components 44. Specifically, as can be seen in FIG. 1, a threaded bore 48, which is sized to receive a corresponding threaded shaft 50 of a stem component 44, is defined in the stem post 60.

The insert 26 is securable to the tibial tray 24. In particular, the insert 26 may be snap-fit to the tibial tray 24. In such a way, the insert 26 is fixed relative to the tibial tray 24 (i.e., it is not rotatable or moveable in the anterior/posterior or medial/lateral directions). Although, in other embodiments, the tibial tray may be secured in a manner that allows it to rotate relative to the tibial tray 24.

The insert 26 includes lateral and medial articulation surfaces 70. The surfaces 70 are configured to articulate with the corresponding articulation surfaces 36 of the femoral component 20. Specifically, the femoral component 20 is configured to be implanted into a surgically-prepared distal end of the patient's femur (not shown), and is configured to emulate the configuration of the patient's natural femoral condyles. As such, the articulation surfaces 36 of the femoral component 20 are configured (e.g., curved) in a manner which mimics the condyles of the natural femur.

As shown in FIG. 1, the stem components 44 of the system 10 include elongated stems 80, which are configured to be attached to either of the components 20, 22. Each elongated stem 80 extends from the threaded shaft 50 at one end to a pointed tip 82 at the opposite end. Each stem also includes a ribbed outer surface 84 extending from the pointed tip 82 toward the threaded shaft 50. A plurality of substantially planar surfaces 86 are positioned around the outer circumference of the stem 80 adjacent to the shaft 50. The surfaces 86 are sized and positioned to receive the end of a wrench or other installation tool so that the stem 80 may be rotated into tight engagement with one of the threaded bores 48.

In the illustrative embodiment, the prosthetic components 12 also include a plurality of offset adapters 90, 92 configured to be attached to the components 20, 22. As shown in FIG. 1, the adapter 90 is configured to offset the longitudinal axis of the elongated stem 80 from the longitudinal axis of the stem post 60 of the tibial tray 24 by a predetermined amount. Similarly, the adapter 92 is configured offset the longitudinal axis of the elongated stem 80 from the longitudinal axis of the stem post 40 of the femoral component 20. Each of the adapters 90, 92 includes a threaded shaft 50 configured to be received in the threaded bore 48 of either of the components 20, 22. Each of the adapters 90, 92 also includes a threaded bore 48 at its opposite end, which is sized to receive a threaded shaft 50 of one of the elongated stems 80. In the illustrative embodiment, a locking nut 100 is positioned on the threaded shaft 50 of each of the adapters 90, 92. The locking nut 100 may be typed against the surface of the stem post of each component to secure the adapter thereto.

The components of the knee prosthesis 10 that engage the natural bone, such as the femoral component 20, the tibial tray 24, and the stem components 44, may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The insert 26 may be constructed with a material that allows for smooth articulation between the insert 26 and the femoral component 20, such as a polymeric material. One such polymeric material is polyethylene such as ultrahigh molecular weight polyethylene (UHMWPE).

Figure 2:
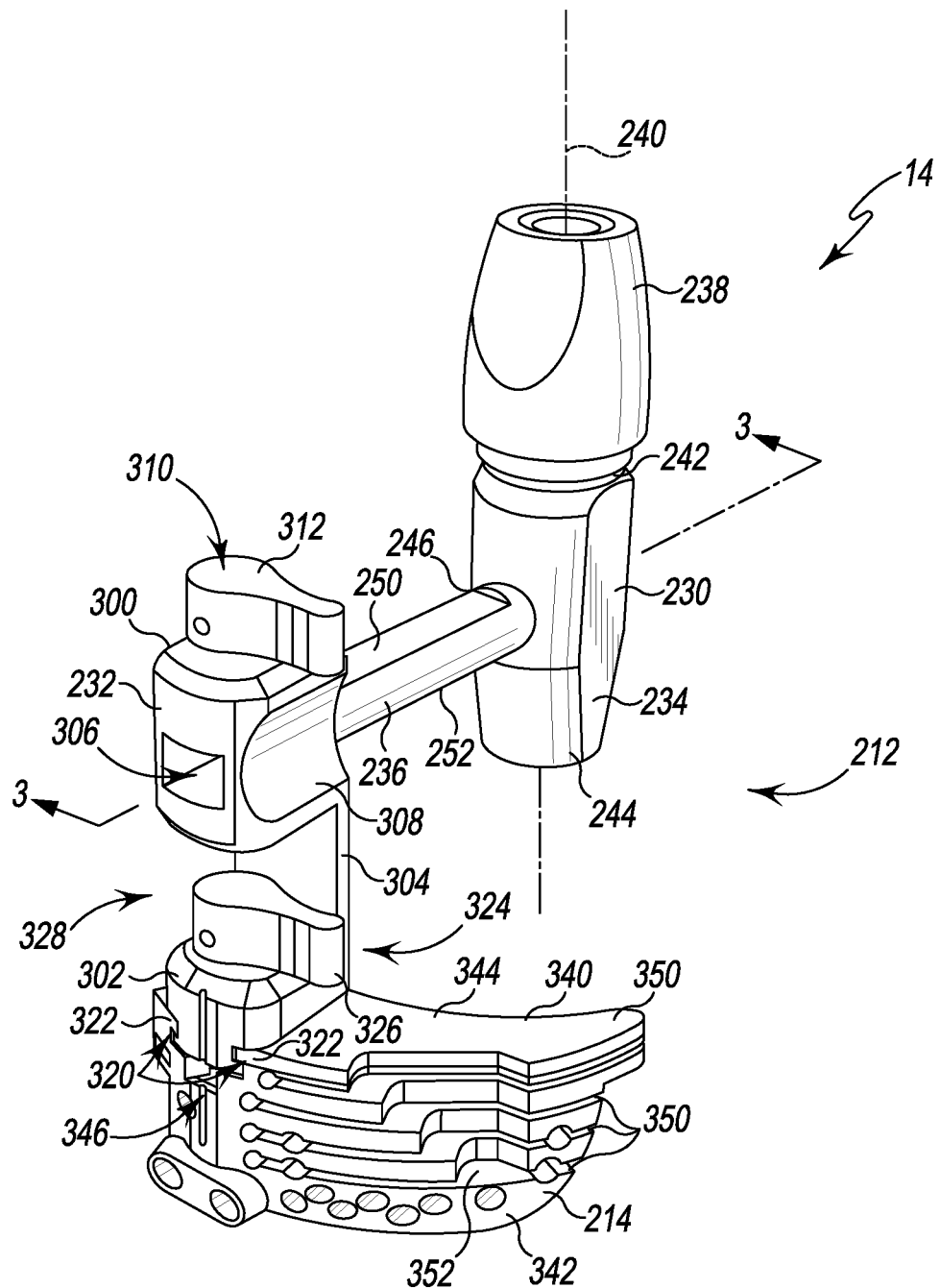
FIG. 2 is a perspective view of a tibial cutting guide assembly of the orthopaedic joint replacement system.

Referring now to FIG. 2, the system 10 includes an attachment device 212 and a cutting block 214 configured to be secured to the attachment device 212. In the illustrative embodiment, the attachment device 212 is configured to be selectively attached to a surgical reamer 216 (see FIG. 4). As described in greater detail below, the surgeon may use the attachment device 212 and the reamer 216 to position the cutting block 214 for use during the resection of the proximal end of a patient's tibia.

The attachment device 212 of the system 10 includes an attachment base 230 configured to be secured to the surgical reamer 216 and a mounting frame 232 configured to be moveably coupled to the base 230. The mounting frame 232 is also configured to be secured to the cutting block 214, as described in greater detail below. In the illustrative embodiment, the attachment base 230 and the mounting frame 232 are formed from a metallic material, such as, for example, stainless steel or cobalt chromium. It should be appreciated that in other embodiments the attachment base 230 or the mounting frame 232 may be formed from a polymeric material.

The attachment base 230 includes a housing 234, a rail 236 that extends outwardly from the housing 234, and a locking knob 238 that is attached to the upper end 242 of the housing 234. The attachment base 230 has a longitudinal axis 240 extending through a lower end 244 and the upper end 242. The rail 236 has an end 246 secured to the housing 234 and extends to a cantilevered tip (see FIG. 3). In the illustrative embodiment, the rail 236 extends orthogonal to the longitudinal axis 240 of the housing 234. As shown in FIG. 2, the rail 236 has an oblong cross-section with a substantially planar top and bottom surfaces 250, 252, respectively, to permit relative rotation between the attachment base 230 and the mounting frame 232.

Figure 3:
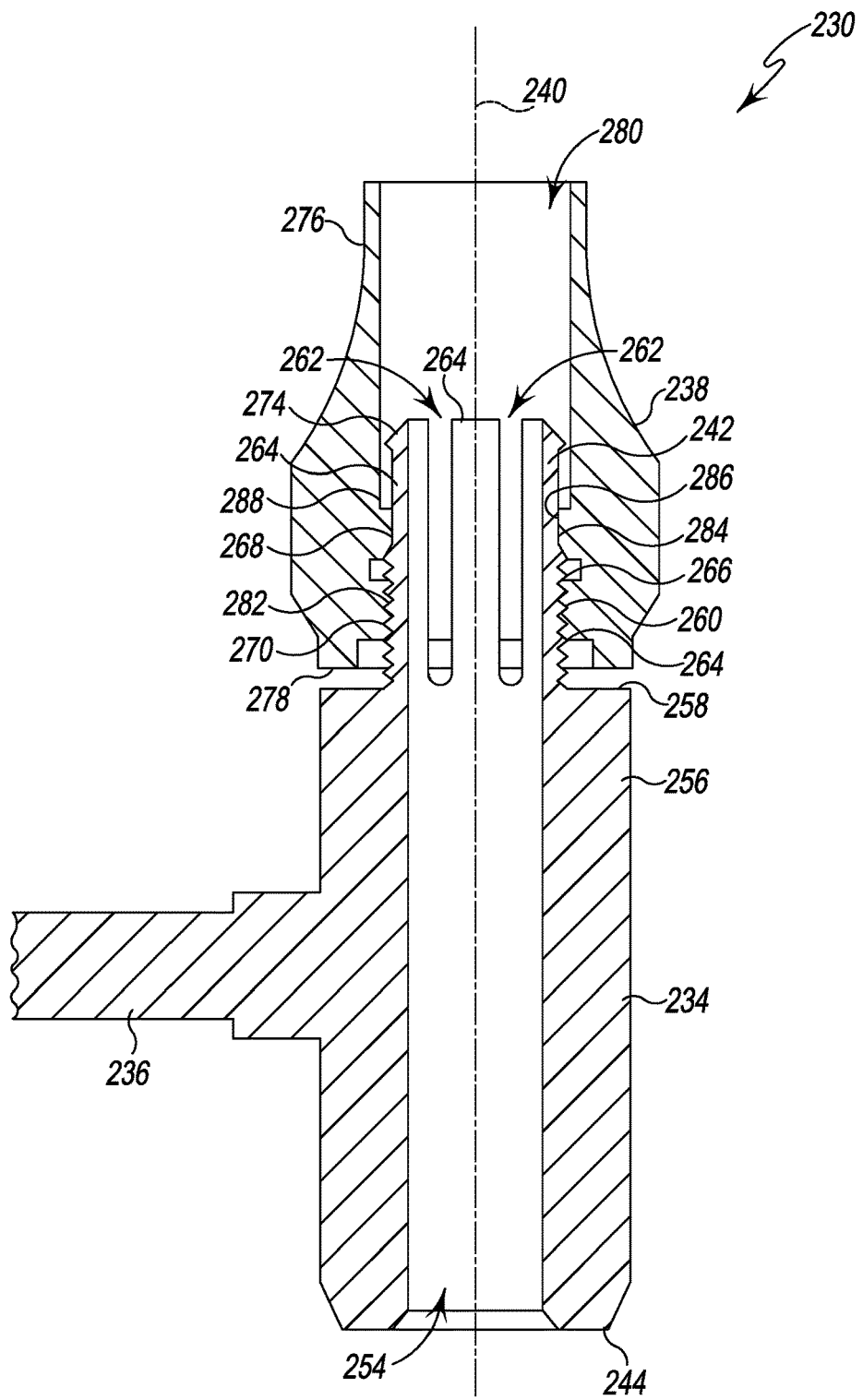
FIG. 3 is a cross-sectional side elevation view of a portion of the cutting guide assembly of FIG. 2 taken along line 3-3 in FIG. 2.

Referring now to FIG. 3, the attachment base 230 has a passageway 254 that extends along the axis 240 from the lower end 244 of the housing 234 through the locking knob 238. The passageway 254 is sized to receive the surgical reamer 216 and permit the base 230 to be moved along the shaft of the reamer 216 to a desired location. The housing 234 includes a main body 256 that extends from the lower end 244 to a shoulder surface 258 positioned below the knob 238. An upper shaft 260 extends outwardly from the shoulder surface 258 to the upper end 242 of the housing 234, as shown in FIG. 3.

In the illustrative embodiment, the upper shaft 260 includes a plurality of longitudinal slots 262 that divide the shaft 260 into a number of beams 264. Each beam 264 includes an outer plate 266 positioned on its outer surface. As shown in FIG. 3, each plate 266 includes an upper surface 268 that is connected to a lower surface 270 that is externally-threaded. When viewed in cross-section, the upper surface 268 is angled or ramped relative to the lower surface 270 so that the plate 266 has an outer diameter at its lower end greater than at its upper end. At the upper end 242, a retaining flange 274 extends outwardly from each of the beams 264.

As shown in FIG. 3, the locking knob 238 includes an upper surface 276 configured to be gripped by a user and a substantially planar bottom surface 278 configured to engage the shoulder surface 258 of the housing 234. A bore 280 extends through the locking knob 238 along the longitudinal axis 240 and defines a section of the passageway 254. In the illustrative embodiment, the locking knob 238 includes an annular rib 282 that extends into the bore 280 near the lower end thereof. The locking knob 238 includes another annular rib 284 that is spaced from and positioned above the rib 282. The annular rib 282 is internally-threaded and may be threaded onto the lower surfaces 270 of the beams 264 of the base 230. As shown in FIG. 3, the annular rib 284 has a conical lower surface 286 such that its inner diameter is greater at its upper end than at its lower end. The rib 284 has an upper surface 288 positioned opposite the lower surface 286. In the illustrative embodiment, the retaining flanges 274 of the beams 264 are configured to engage the upper surface 288 to prevent the disassembly of the knob 238 from the housing 234.

In use, a surgeon may position a reamer 216 in the passageway 254 of the attachment base 230. To lock the base 230 in position relative to the reamer 216, the surgeon may rotate the knob 238 clockwise about the axis 240 to slide the ribs 282, 284 downward along the plates 266 of the beams 264. The engagement between the conical lower surface 286 of the rib 284 and the ramped upper surfaces 268 of the beams 264 causes the beams 264 to bend radially inward toward the axis 240, thereby contracting the diameter of the passageway 254. In the illustrative embodiment, when the bottom surface 278 of knob 238 is engaged with the shoulder surface 258 of the housing 234, the beams 264 are compressed against the reamer 216, thereby securing the attachment base 230 to the reamer 216 at a desired position. To release the attachment base 230, the surgeon may rotate the knob 238 counterclockwise and advance the knob 238 upward, thereby moving the rib 284 out of contact with the plates 266 and permitting the beams 264 bend radially outward.

Returning to FIG. 2, the system 10 also includes a mounting frame 232 configured to be moveably coupled to the base 230. In the illustrative embodiment, the mounting frame 232 includes an upper bracket 300, a lower bracket 302, and a base plate 304 connecting the brackets 300, 302. The upper bracket 300 includes an opening 306 sized to receive the rail 236 of the attachment base 230. In the illustrative embodiment, the opening 306 is defined by a pair of substantially planar surfaces that match the configuration of the surfaces 250, 252 of the rail 236. A knurled surface 308 is positioned on each side of the bracket 300 to permit a surgeon to grip the bracket 300 to advance it along the rail 236.

The upper bracket 300 also includes a locking mechanism 310, which may be operated to secure the upper bracket (and hence the mounting frame 232) to the rail 236. In the illustrative embodiment, the locking mechanism 310 includes a user-operated handle 312 and a shaft (not shown) that extends through a bore into the opening 306. When the handle 312 is rotated clockwise, the shaft 314 is advanced into engagement with the upper surface 250 of the rail 236. It should be appreciated that in other embodiments other mechanical locking devices may be used to secure the mounting frame 232 in position relative to the rail 236.

As described above, the mounting frame 232 also includes a lower bracket 302. The lower bracket 302 includes a pair of grooves 320 sized to receive a corresponding pair of tabs 322 of the cutting block 214. In that way, the grooves 320 provide a mounting point for the cutting block 214. Similar to the upper bracket 300, the lower bracket 302 includes a locking mechanism 324, which may be operated to secure the cutting block 214 to the lower bracket 302. In the illustrative embodiment, the locking mechanism 324 includes a user-operated handle 326 that is positioned in a gap 328 defined between the brackets 300, 302. The handle 326 is attached to a shaft (not shown). When the handle 326 is rotated clockwise, the shaft may be advanced into engagement with the cutting block 214, thereby securing the block 214 to the mounting frame 232. It should be appreciated that in other embodiments other mechanical locking devices may be used to secure the mounting frame 232 to the cutting block 214.

As shown in FIG. 2 the cutting block 214 includes a posterior side wall 340 that is configured to confront the anterior side of the patient's tibia, as described in greater detail below. The cutting block 214 also includes an anterior side wall 342 that is positioned opposite the posterior side wall 340. An upper surface 344 connects the side walls 340, 342. The upper surface 344 has a groove 346 defined between the tabs 322 described above. In the illustrative embodiment, the cutting block 114 is formed from a metallic material, such as, for example, stainless steel or cobalt chromium.

The cutting block 214 includes a number of cutting guides 350 that may be used during an orthopaedic surgical procedure to resect a portion of the patient's bone. Each cutting guide 350 includes an elongated slot sized to receive a cutting saw blade of a surgical saw or other surgical device. In the illustrative embodiment, the cutting block 214 has four cutting guides 350 extending through the side walls 340, 342. Each cutting guide 350 is spaced apart from the other cutting guides 350 by about 5 millimeters and includes a planar surface 352 that defines a resection plane.

Figure 4:
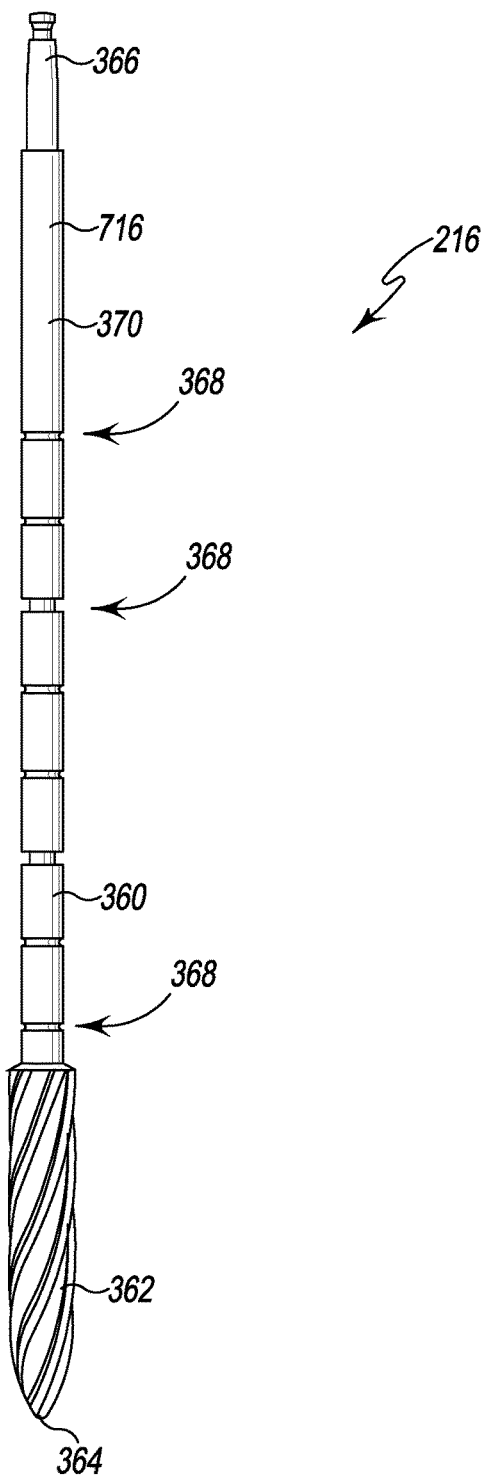
FIG. 4 is a side elevation view of a surgical reamer of the orthopaedic joint replacement system.

As described above, the system 10 includes a number of surgical reamers to define a passageway in the patient's tibia during the surgical procedure. Referring now to FIG. 4, one of the surgical reamers 216 is shown. The reamer 216 includes an elongated shaft 360 having a plurality of cutting flutes 362 formed at a distal end 364. A tool shank 366 is formed at the opposite end and is sized to be secured to a surgical drill or other rotary surgical instrument. The elongated shaft 360 includes a cylindrical outer surface 370 that extends from the cutting flutes 362 to the tool shank 366. A plurality of spaced-apart annular slots 368 are defined in the outer surface 370. In the illustrative embodiment, the position of each annular slot 368 along the outer surface 370 corresponds to a desired reaming depth of the reamer 216. In the illustrative embodiment, the heights of the slots 368 vary in order to provide the surgeon with a visual indication of the different depths.

Figure 5:
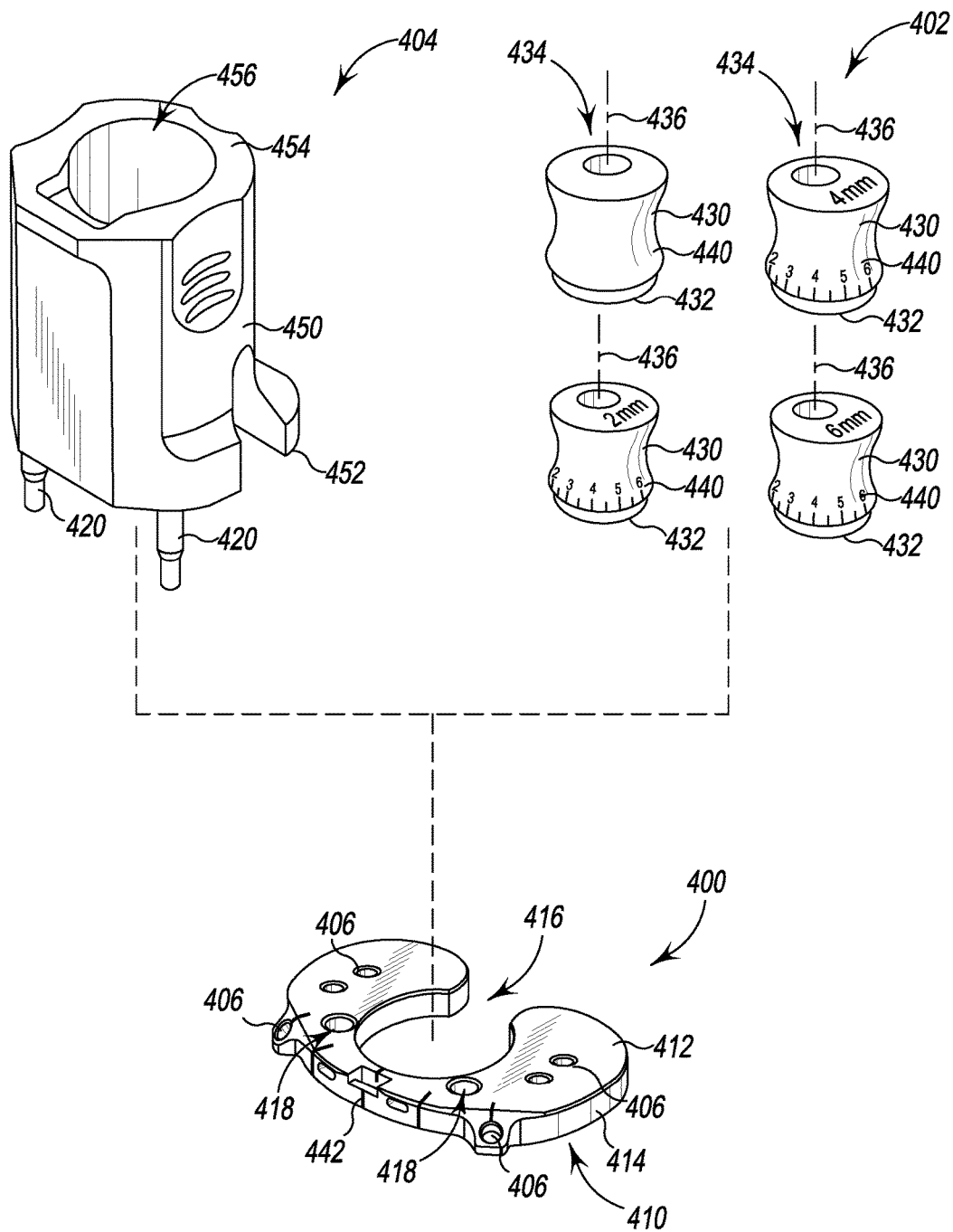
FIG. 5 is an exploded perspective view of a number of surgical instruments of the orthopaedic joint replacement system for use in determining an amount of tibial offset.

Referring now to FIG. 5, the system 10 also includes a tibial base plate 400 configured to be positioned on a proximal end of a patient's tibia. It should be appreciated that the system 10 may include multiple tibial plates of different sizes generally corresponding to the various potential sizes of a patient's bony anatomy. The system 10 also includes a plurality of offset guides 402 configured for use with the tibial base plate 400 and a reaming guide tower or body 404 that is also configured for use with the tibial plate 400. The tibial base plate 400 includes a number of fixation pin guide holes 406, which permit the passage of fixation pins 408 (see FIG. 21) to secure the tibial plate 400 to the proximal end of the patient's tibia.

The tibial base plate 400 includes a substantially planar bottom surface 410 and a substantially planar top surface 412 that is positioned opposite the bottom surface 410. A curved outer side wall 414 extends between the surfaces 410, 412. The tibial plate 400 also includes a central opening 416 that extends through the surfaces 410, 412. A pair of guide bores 418 are positioned adjacent to the anterior side of the tibial plate 400. As described in greater detail below, each guide bore 418 is sized to receive one of the fixation pins 420 of the reaming guide tower 404.

As shown in FIG. 5, each offset guide 402 includes an upper drum 430 connected to a lower cylindrical plate 432. The cylindrical plate 432 is sized to be received in the central opening 416 of the tibial plate 400. Each offset guide 402 also includes a passageway 434 that extends through the drum 430 and plate 432. The amount of offset is different for each offset guide 402. In the illustrative embodiment, the drum 430 includes a plurality of indicia 440 that cooperate with a marking 442 on the tibial base plate 400 to provide a surgeon with an indication of the angular position of the longitudinal axis 436. When the marking 442 is aligned with one of the indicia 440, a numerical indicator corresponding to that indicia 440 may be read to determine the offset orientation.

Figure 5A:
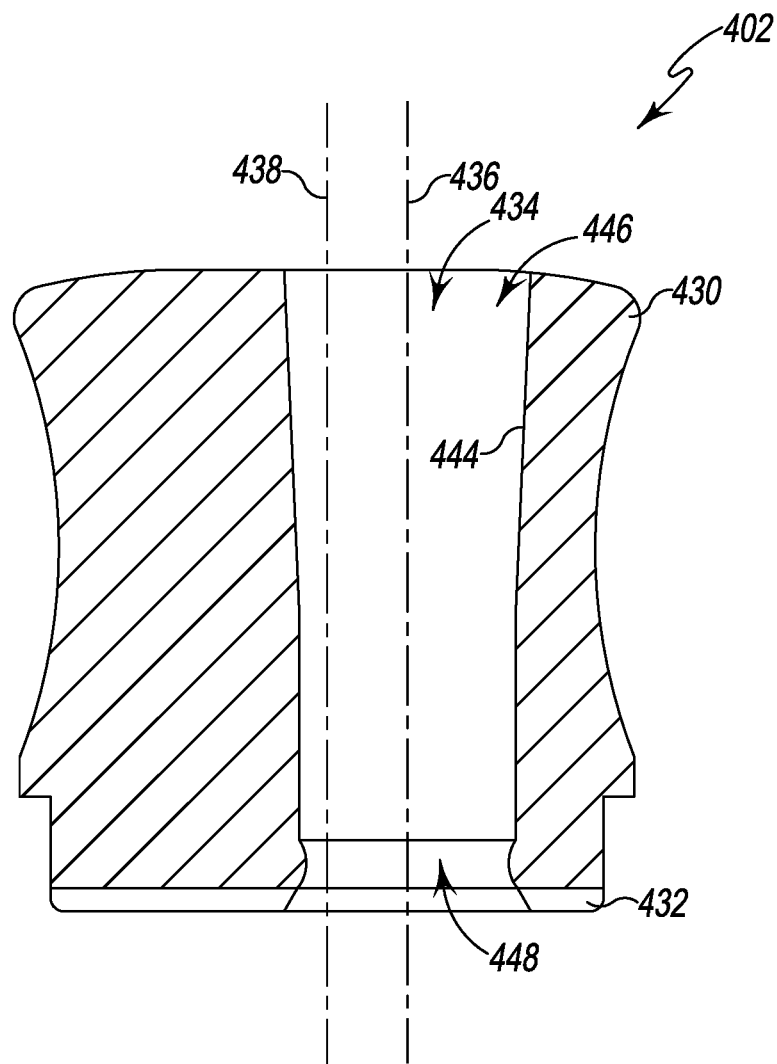
FIG. 5A is a cross-sectional elevation view of an offset guide of the surgical instruments of FIG. 5.

As shown in FIG. 5A, each passageway 434 extends along a longitudinal axis 436 that is offset from the longitudinal axis 438 of the cylindrical plate 432. In the illustrative embodiment, the elongated shaft 360 of the reamer extends longitudinal axis 438 when the tibial base plate 400 is positioned over the reamer. The passageway 434 is illustratively defined by a tapered inner wall 444 that extends from an upper or proximal opening 446 that is larger than the lower or distal opening 448. In other embodiments, the passageway may be cylindrical.

As described above, the system 10 also includes a reaming guide tower 404. The tower 404 includes a main body 450 that extends from a substantially planar bottom surface 452 to an upper surface 454. A guide passageway 456 extends through the surfaces 452, 454. When the tower 404 is attached to the tibial plate 400, the passageway 456 is aligned with the central opening 416. As described above, the tower 404 includes a pair of anterior fixation pins 420, which are received in the anterior bores 418 of the tibial plate 400 when the tower is attached thereto.

Figure 6:
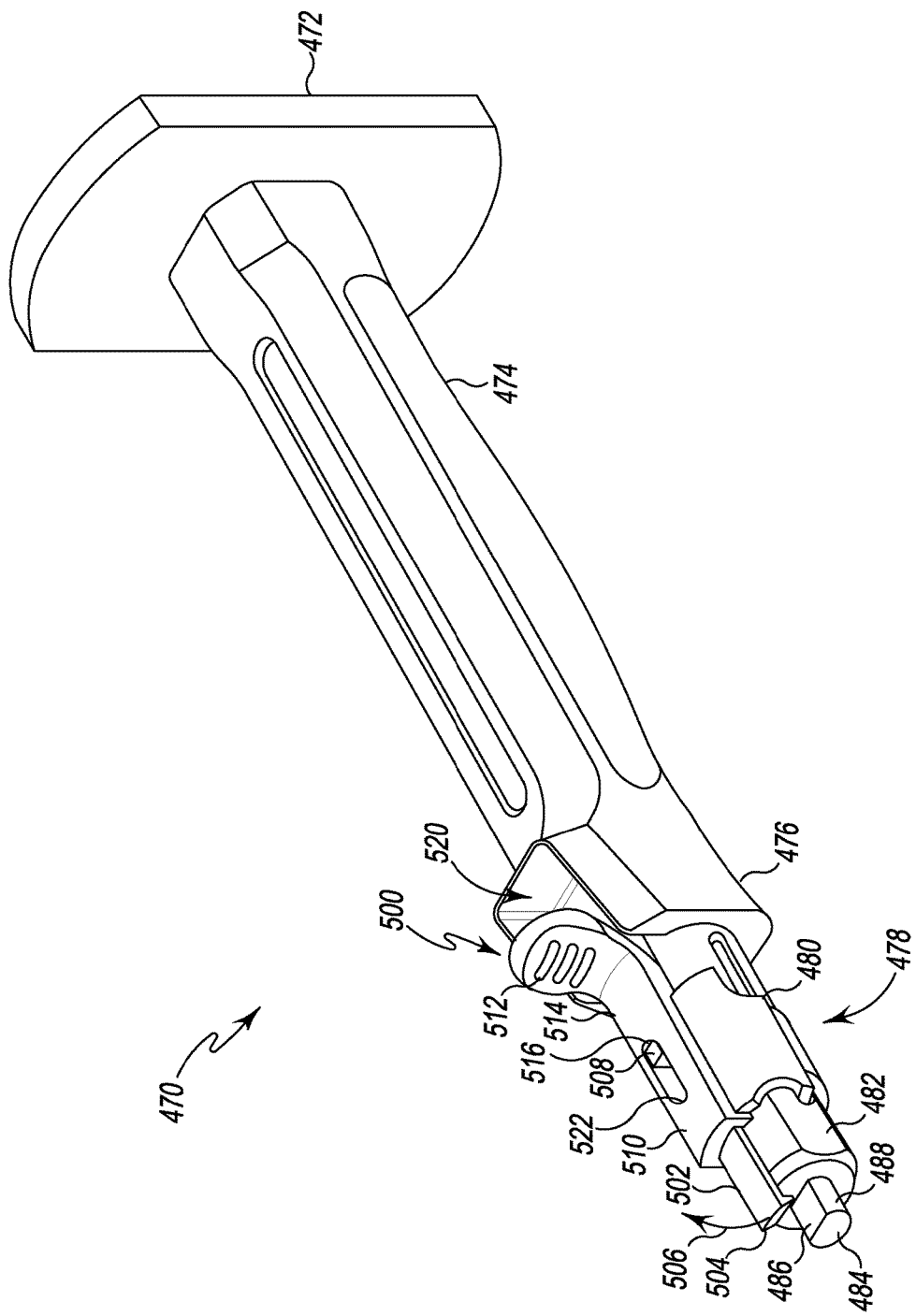
FIG. 6 is a perspective view of an impaction handle of the orthopaedic joint replacement system.

Referring now to FIG. 6, an impaction handle 470 of the system 10 is shown. In the illustrative embodiment, the impaction handle is formed as an assembly from separate components made from metallic materials such as, for example stainless steel. The impaction handle 470 includes a strike plate 472 attached to the distal end of an elongated body 474. The elongated body 474 is sized and shaped to be gripped by a surgeon during use. The body 474 extends from the strike plate 472 to an end 476. The impaction handle 470 also includes a proximal post 478 that extends from the end 476 of the elongated body 474. The proximal post 478 includes a cylindrical body section 480 that is connected to the end 476, an intermediate cylindrical body section 482 extending from the body section 480, and a proximal tip 484 extending from the section 482. The proximal tip 484 includes a substantially planar anterior surface 486 that is connected to a curved posterior surface 488.

The impaction handle 470 includes an attachment mechanism 500 configured to selectively secure other surgical instruments to the impaction handle 470 during the surgical procedure. In the illustrative embodiment the attachment mechanism 500 includes a lever arm 502, which is coupled to the post 478 and is configured to pivot relative to the proximal post 478. The lever arm 502 includes a locking flange 504 that extends toward the planar anterior surface 486 of the proximal tip 484. When the lever arm 502 is pivoted in the direction indicated by arrow 506, the locking flange 504 is advanced away from the proximal tip 484. The lever arm 502 also includes a tab 508 that extends in the direction opposite the locking flange 504.

The attachment mechanism 500 includes a bracket 510 that is configured to slide relative to the post 478 and the elongated body 474. The bracket 510 is illustratively L-shaped and includes a flange 512 that extends away from the proximal post 478. The flange 512 is connected to a slide plate 514 that extends along the body section 480. As shown in FIG. 6, the slide plate 514 has an oblong slot 516 defined therein, and the tab 508 is positioned in the slot 516.

Figure 6A:
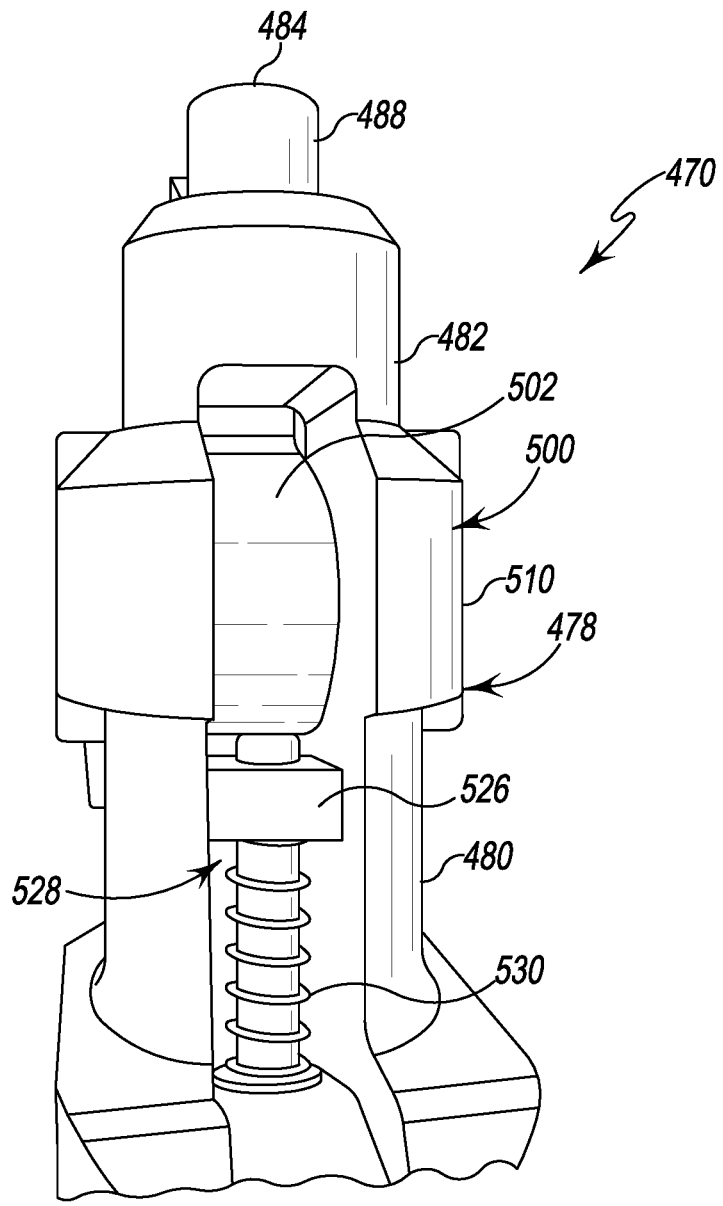
FIG. 6A is a bottom perspective view of the impaction handle of FIG. 6.

The bracket 510 includes a pair of tabs 522 that are received in a pair of longitudinal slots 524 defined in the cylindrical body section 480 of the post 478. As shown in FIG. 6A, the bracket 510 also includes a plate 526 that is received in a channel 528 extending through the post 478. A biasing element such as, for example, a spring 530 is positioned between the plate 526 and the post 478 to bias the bracket 510 (and hence the lever arm 502) in the position shown in FIG. 6.

To advance the lever arm 502 in the direction indicated by arrow 506, a user may press on the flange 512 to overcome the bias exerted by the spring 530 and cause the bracket 510 to advance distally toward the strike plate 472. As the bracket 510 advances distally, the flange 512 is advanced into a channel 520 defined in the end 476 of the elongated body 474. Additionally, the proximal edge 522 of the slide plate 514 is advanced into engagement with the tab 508, thereby causing the lever arm 502 to pivot about its axis 532 (see FIG. 6A) and moving the locking flange 504 away from the proximal tip 484. When the user releases the flange 512, the spring 530 urges the slide plate 514 toward the proximal end, thereby releasing the lever arm 502 to pivot toward the locking flange 504.

Figure 7:
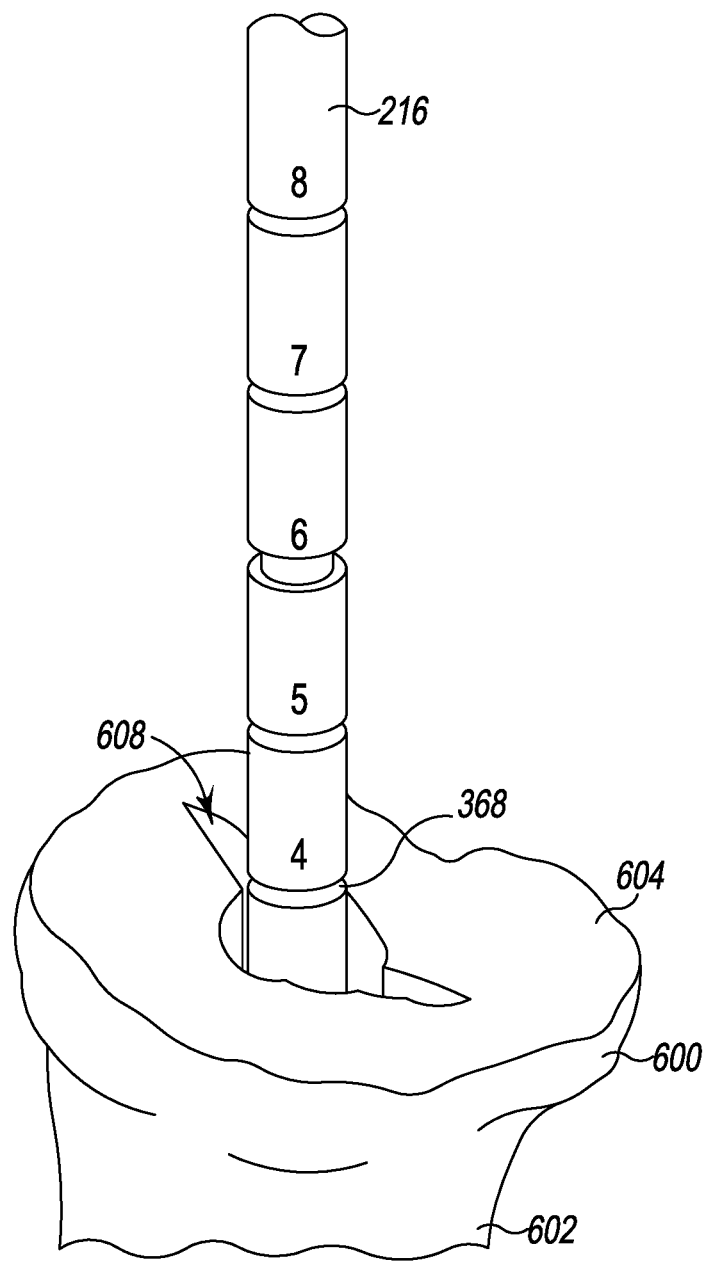
FIGS. 7-21 illustrate a number of steps of a surgical procedure utilizing the orthopaedic joint replacement system.

The instruments 14 described may be used to surgically prepare a patient's femur to receive a prosthetic tibial component 22, one of the stem components 44, and an offset adaptor 90. In the illustrative embodiment, the instruments 14 may be used in a revision procedure in which a primary implant has been removed from a proximal end of the patient's tibia. As shown in FIG. 7, the proximal end 600 of a patient's tibia 602 in a revision procedure includes a proximal surface 604 that has been previously-shaped to receive the primary implant. During a revision procedure, the surface 604 is resected to prepare the proximal end 600 to receive the prosthetic tibial component 22. FIGS. 7-23 illustrate a number of exemplary steps of a procedure for surgically-preparing the proximal end 600 during a revision procedure. It should be appreciated that any surgical procedure may include additional or fewer steps depending on the state of the patient's bony anatomy and the preferences of the surgeon.

Referring now to FIG. 7, the surgeon may select one of the reamers 216 for insertion into the intramedullary canal 608 of the patient's tibia 602. The choice of reamer may depend on the size and shape of the patient's tibia 602. As shown in FIG. 7, the surgeon may advance the selected reamer 216 into the canal 608 to straight ream the canal to a predetermined depth corresponding to one of the annular slots 368.

Figure 8:
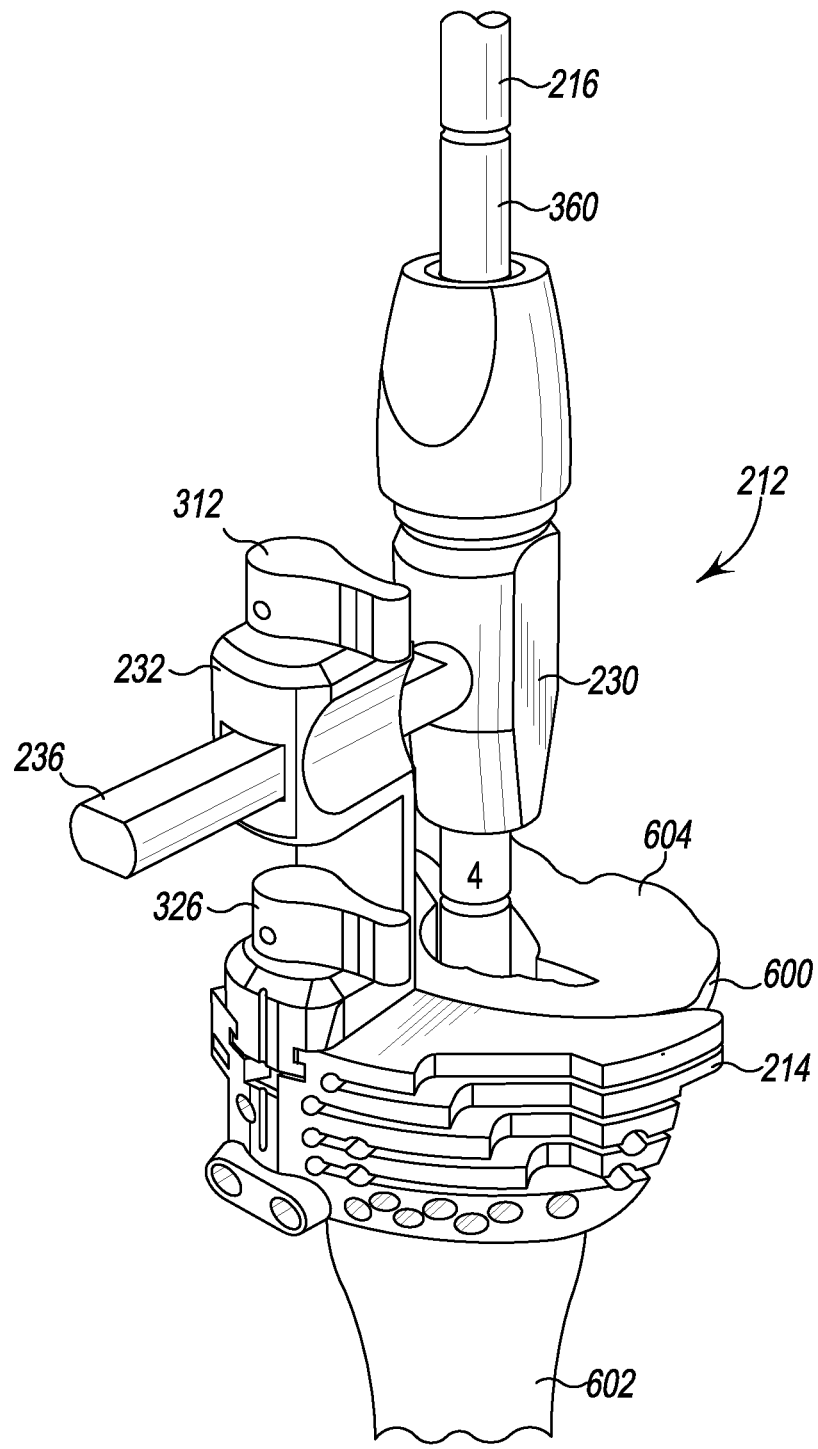

The surgeon may leave the reamer 216 in place at the predetermined depth while assembling the attachment device 212. As described above, the surgeon may attach the cutting block 214 to the mounting frame 232 and securing the instruments together by operating the handle 326. The surgeon may slide the mounting frame 232 along the rail 236 of the attachment base 230 and lock the frame 232 in position relative to the base 230 by operating the other handle 312. As shown in FIG. 8, the surgeon may place the assembled attachment device 212 on the elongated shaft 360 of the reamer 216. To do so, the surgeon may align the passageway 254 of the attachment device 212 with the shank 366 of the reamer 216 and then advance the attachment device 212 over the shank 366 and down the elongated shaft 360 toward the tibia 602.

Figure 9:
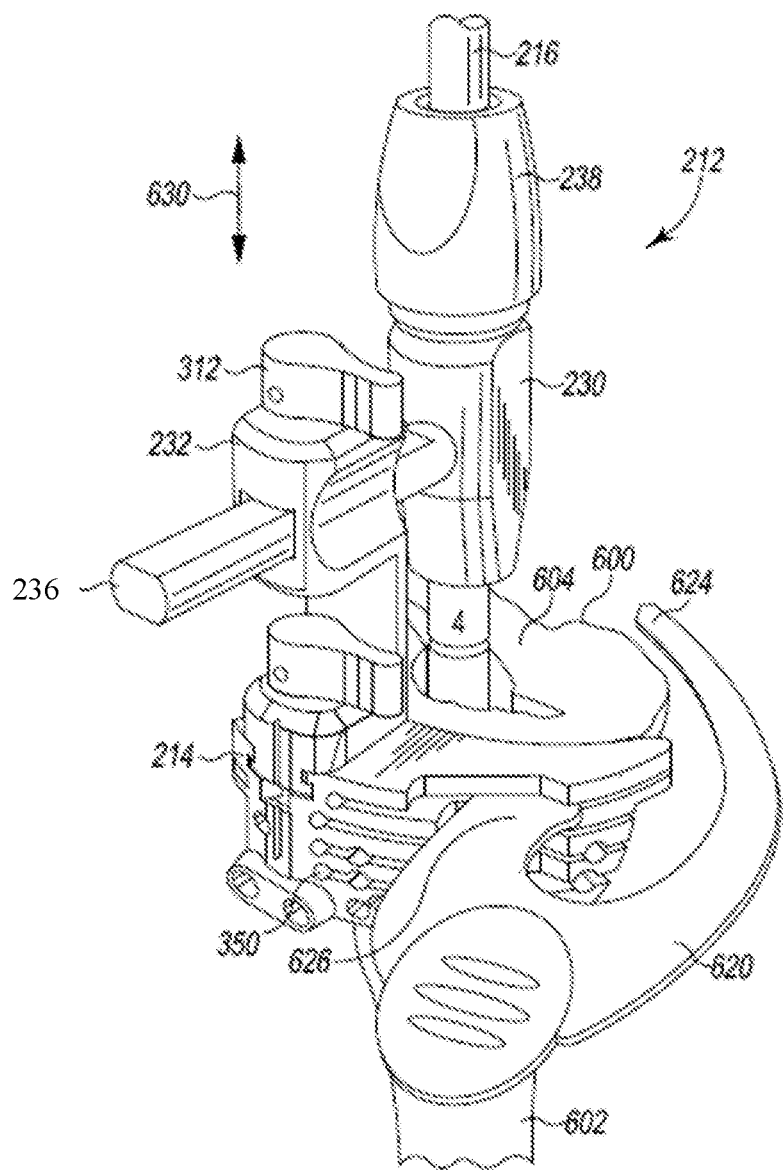
Figure 10:
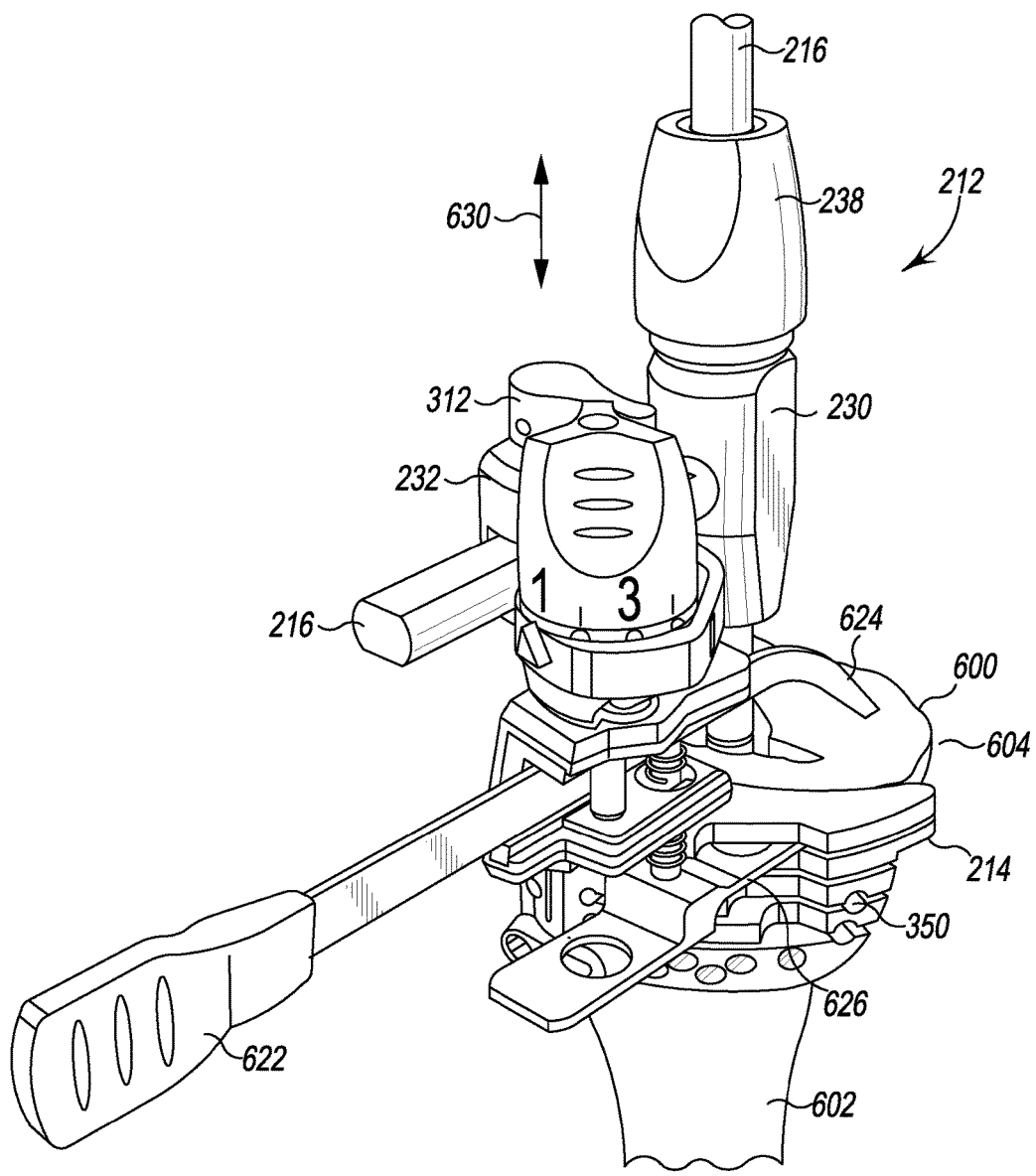

As shown in FIGS. 9-10, a surgeon may utilize a number of different gauges 620, 622 to determine where to place the cutting block 214 relative to the bone 602. Each of the gauges 620, 622 has a probe tip 624 configured to engage the proximal surface 604 when the cutting block 214 is properly positioned relative to the tibia 602. In the illustrative embodiment, each gauge is selectively attached to the cutting block 214 via a mounting flange 626 sized to be positioned in the cutting guides 350 of the block 214. The gauge 622 is also adjustable such that the probe tip 624 may be set at different heights relative to its mounting flange 626 (and hence the cutting block 214). The surgeon may slide the attachment device 212 and cutting block 214 along the reamer 216 in the directions indicated by arrows 630 in FIGS. 9-10 until the cutting block 214 is properly positioned to guide the resection of the proximal surface 604.

The surgeon may then lock the attachment device 212 at the desired position by operating the control knob 238. When the knob 238 is rotated clockwise, the ribs 282, 284 of the knob 238 cause the diameter of the passageway 254 to contract, as described above. In the illustrative embodiment, when the bottom surface 278 of knob 238 is engaged with the shoulder surface 258 of the housing 234, the attachment base 230 engages the reamer 216, thereby locking the cutting block 214 in position relative to the bone. The surgeon may also selectively operate the handle 312 to free the mounting frame 232 (and hence the cutting block 214) for movement along the rail 236. In that way, the surgeon may also adjust the position of the cutting block 214 relative to the anterior face of the tibia 602.

Figure 11:
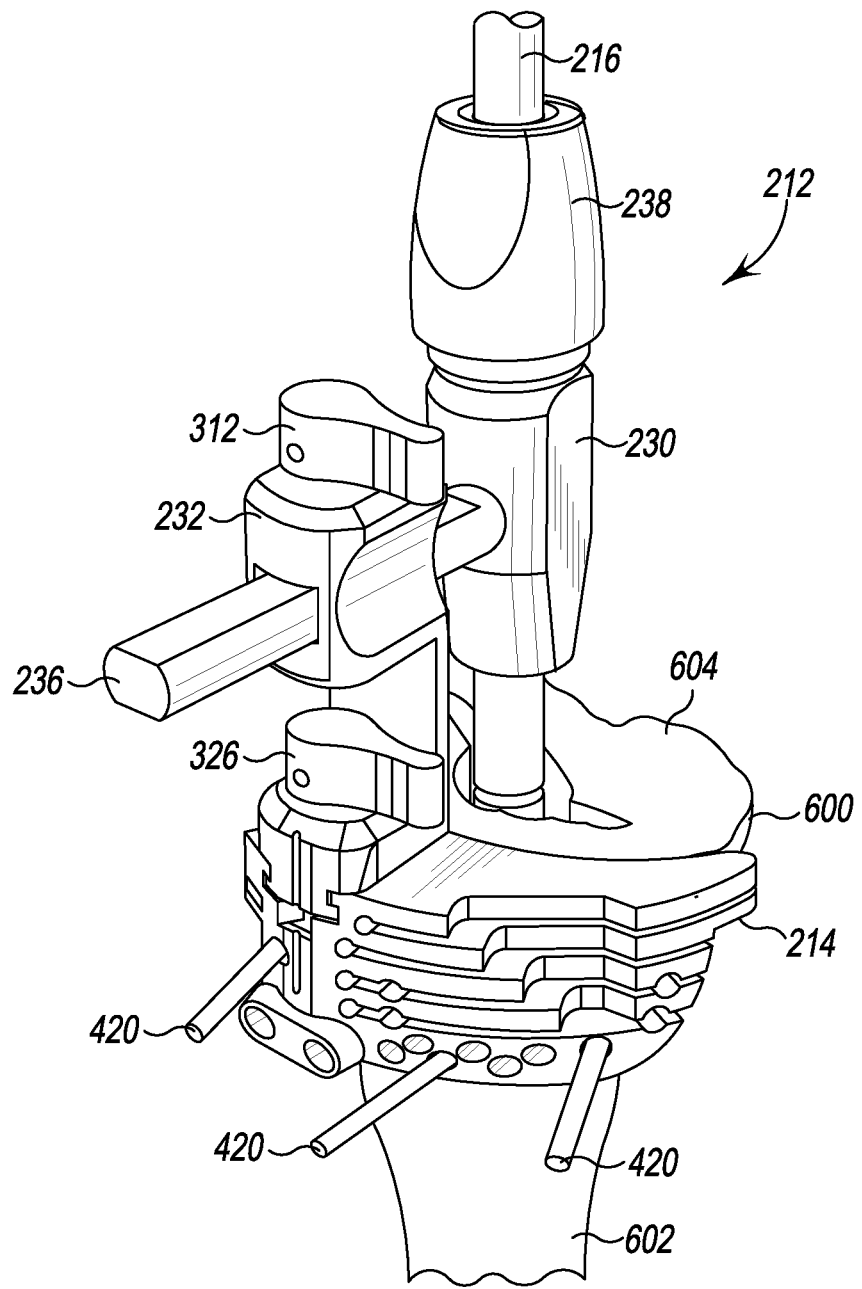

As shown in FIG. 11, the surgeon may utilize a number of fixation pins 420 to secure the cutting block 214 to the tibia 602. The surgeon may then detach the cutting block 214 from the attachment device 212 by operating both handles 312, 326 to release the mounting frame 232 from the cutting block 214 and the attachment base 230. After sliding the mounting frame 232 off the rail 236, the surgeon may release the attachment base 230 from the reamer 216 by operating the control knob 238.

Figure 12:
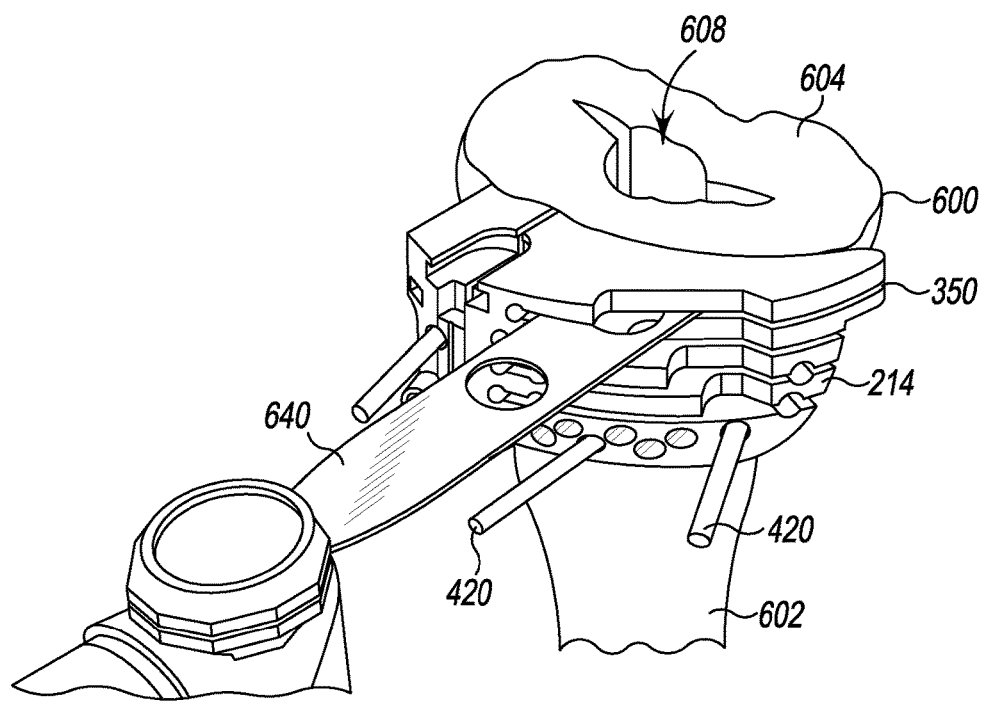

Referring now to FIG. 12, the surgeon may also remove the reamer 216 from the canal 608 before resecting the tibia 602. To perform the resection, the surgeon may advance a surgical saw 640 through one of the cutting guide slots 350 into contact with the patient's bone. The surgeon may then use the saw 640 to remove material from the end 600 of the patient's tibia 602 and create a new surgically-prepared proximal surface shaped to receive a prosthetic tibial component 22.

Figure 13:
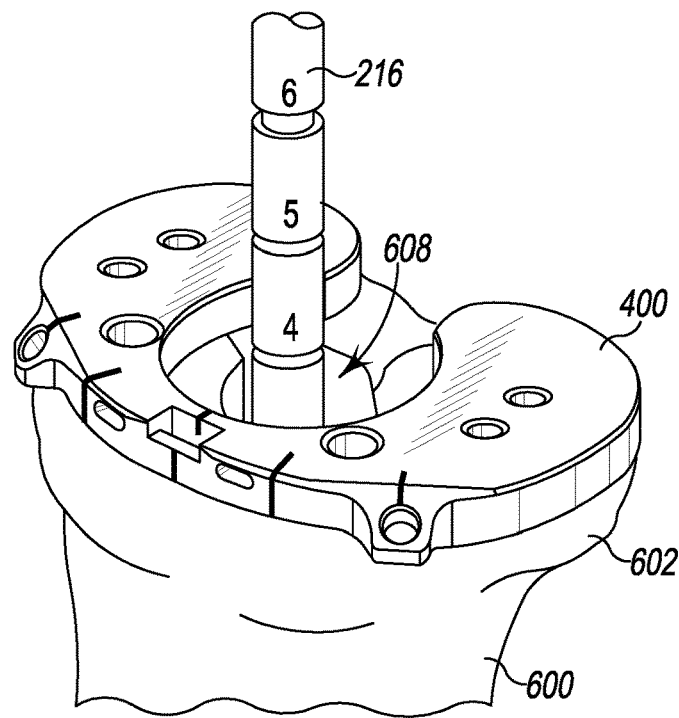
Figure 14:
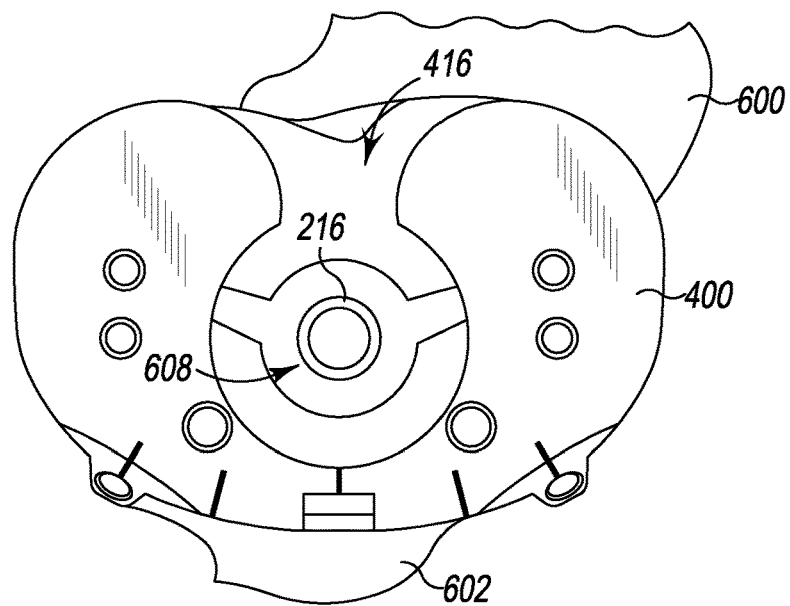

Referring now to FIGS. 13-14, surgeon may utilize the reamer 216 and the tibial plate 400 to determine whether an offset adaptor 90 should be included in the tibial prosthetic assembly. To do so, surgeon may insert the reamer 216 into the intramedullary canal 608, as shown in FIG. 13. The surgeon may position the tibial plate 400 on the proximal end 600 of the patient's tibia 602. As shown in FIG. 14, the center of the opening 416 of the tibial plate 400 is offset from the longitudinal axis of the reamer 216, indicating the need to use an offset adapter 90 in the tibial prosthetic assembly.

Figure 15:
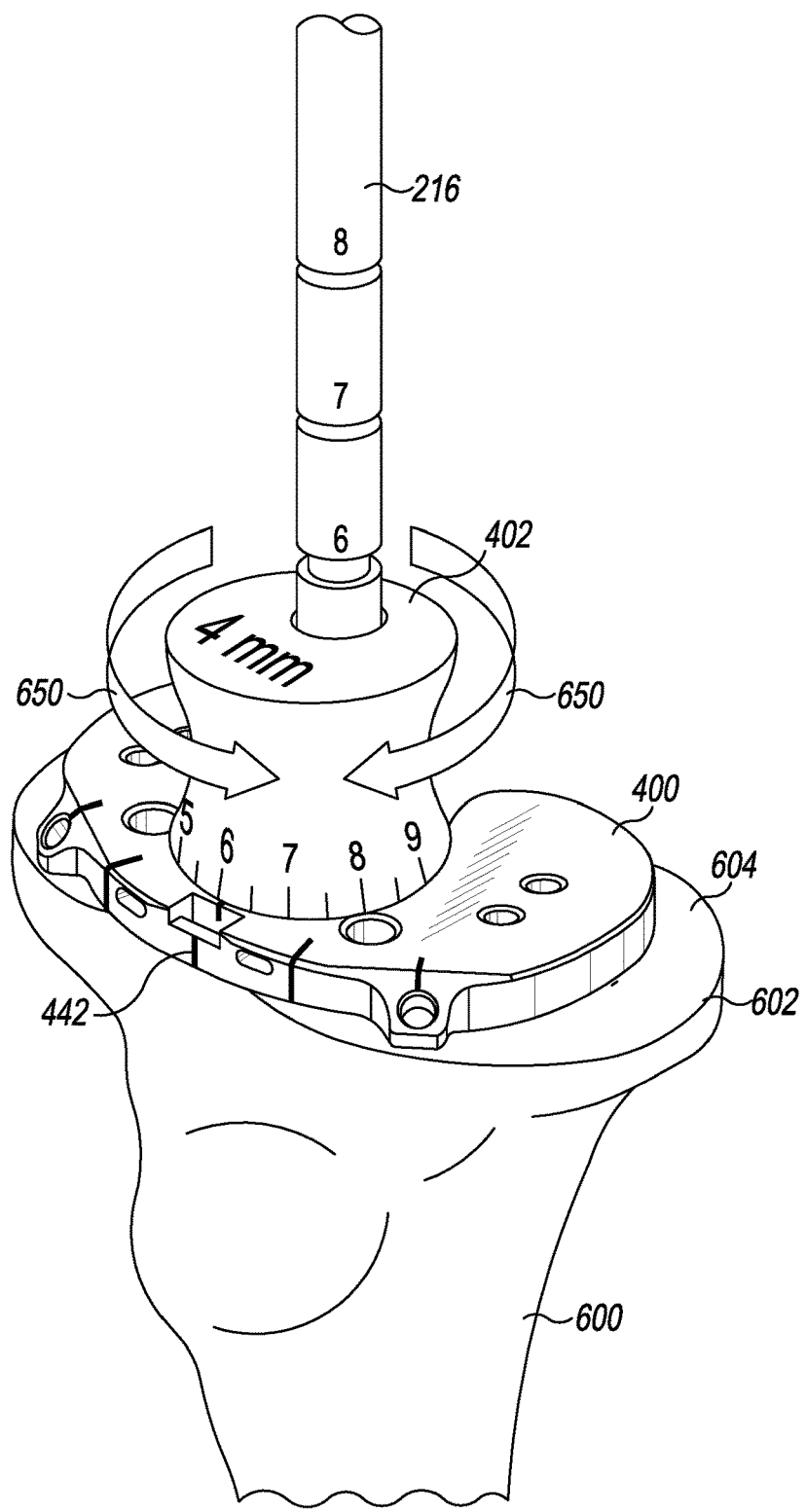
Figures 16, 16A:
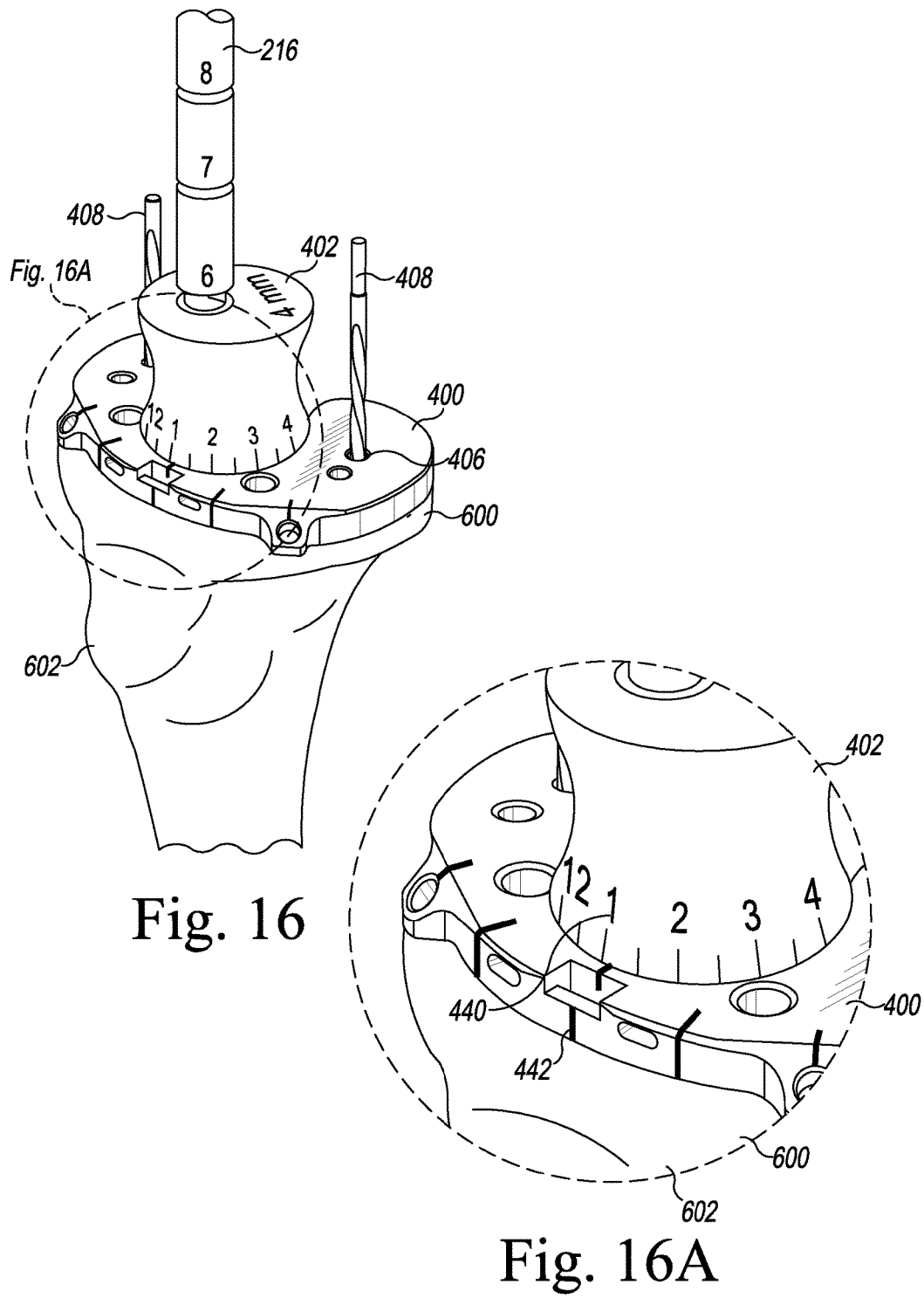
Figure 17:
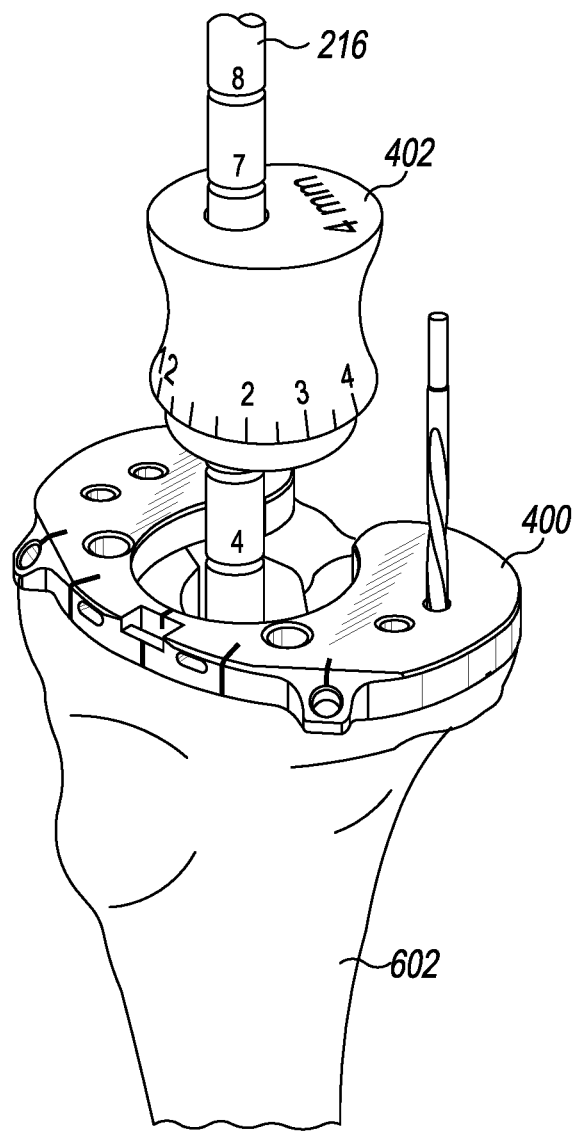

As shown in FIG. 15, the surgeon may select an offset guide 402 and advance along the reamer 216 into contact with the tibial plate 400 positioned on the patient's tibia 602. With the offset guide 402 seated on the tibial plate 400, the surgeon may grip the contoured outer surface of the guide 402 to turn the guide 402 about the reamer 216 as indicated in FIG. 15 by arrows 650. As the guide 402 is turned, the tibial plate 400 is rotated about the proximal surface 604 of the patient's tibia 602. That movement changes the offset orientation of the guide 402 and tibial plate 400 relative to the reamer 216. The surgeon may continue to turn the guide 402 until the tibial plate 400 is placed in a location on the patient's tibia 602 that offers maximum coverage of the surgically-prepared proximal surface 604. When the base plate 400 is in the desired location on the patient's tibia 602, the surgeon identifies the indicia 440 that is aligned with the mark 442 and reads the numerical indicator associated with the indicia 440 to identify the selected offset orientation, as shown in FIG. 16. It should be appreciated that the surgeon may repeat this process with other offset guides 402 having different amounts of offset until the tibial plate 400 is placed in a location on the patient's tibia 602 that offers maximum coverage of the proximal surface 604. When the tibial plate 400 is positioned at a desired location on the patient's tibia 602, the surgeon may utilize one or more fixation pins 408 to secure the tibial plate 400 and the position, as shown in FIG. 16. The surgeon may then remove the offset guide 402 from the tibial plate 400 and the reamer 216, as shown in FIG. 17.

Figure 18:
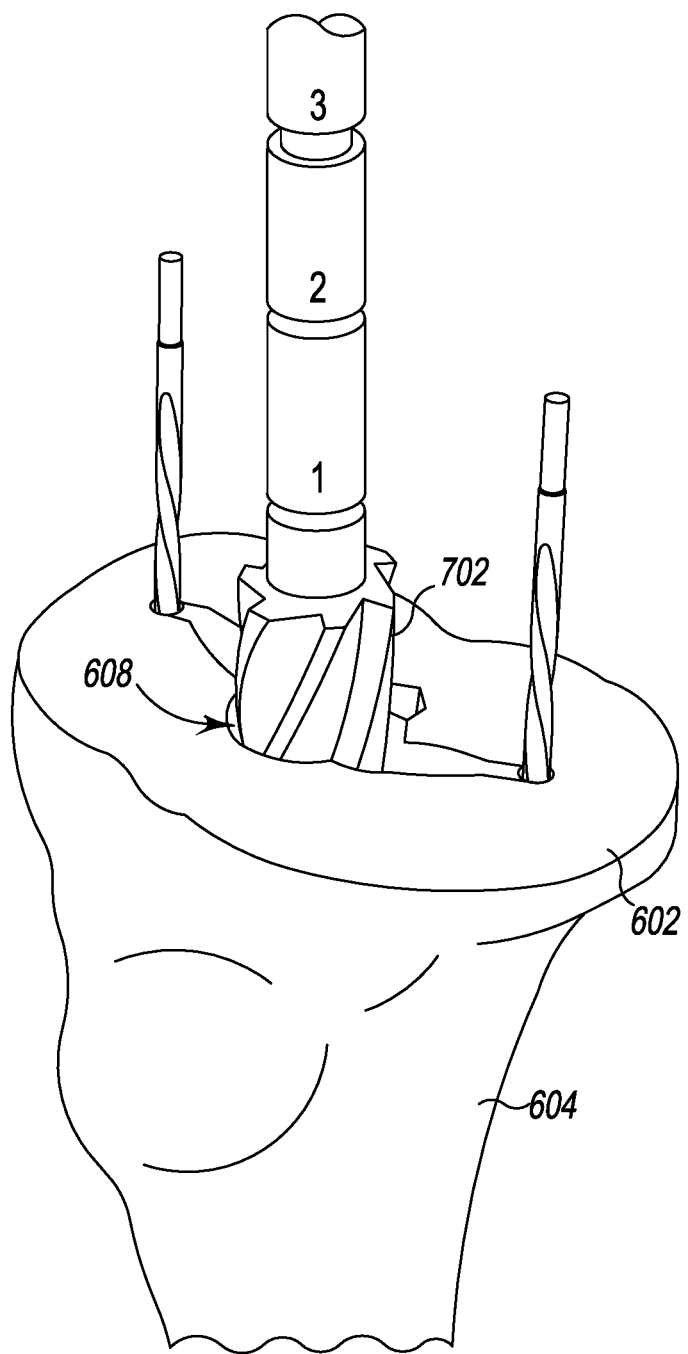
Figure 19:
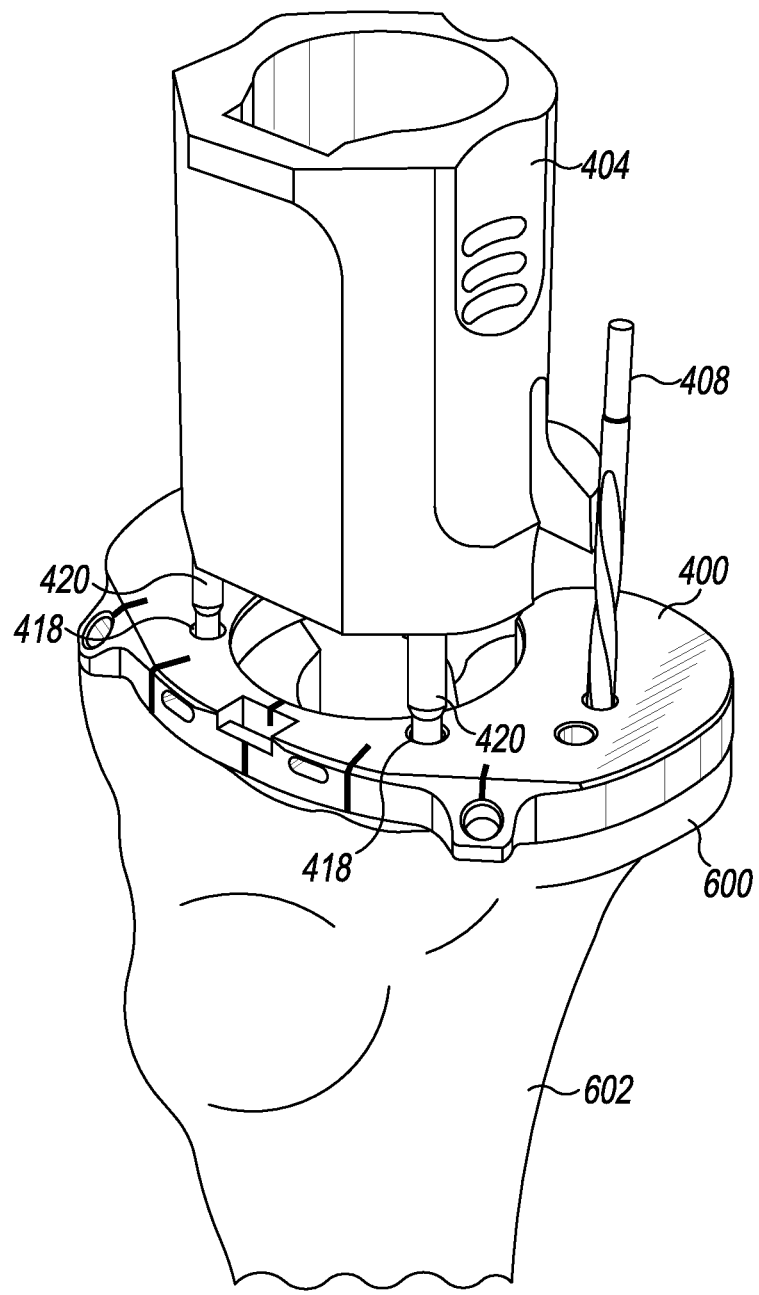

Referring now to FIG. 18, the surgeon may perform another reaming operation utilizing a larger diameter reamer 702 continue reshaping the canal 608. As shown in FIG. 19, the surgeon may also utilize the reaming guide tower 404 with the tibial plate 400. To do so, the surgeon may align the fixation pins 420 of the tower 404 with the guide holes 418 of the tibial plate 400. The surgeon may then advance the fixation pins 420 through the guide holes 418 and into the proximal end 600 of the patient's tibia 602.

Figure 20:
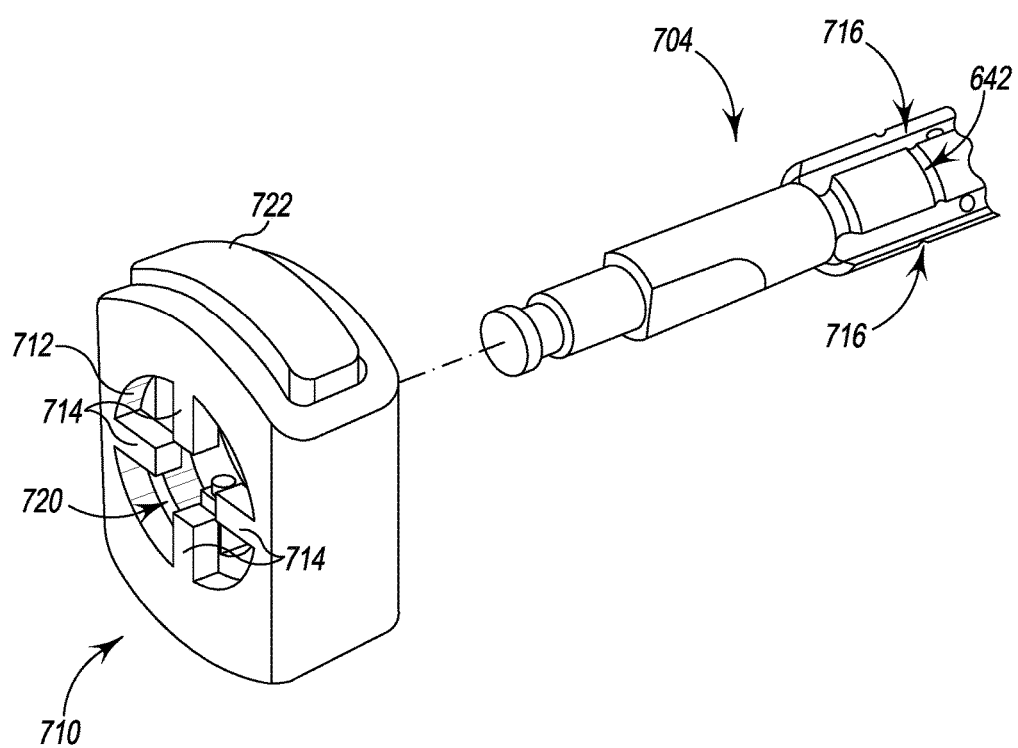
Figure 21:
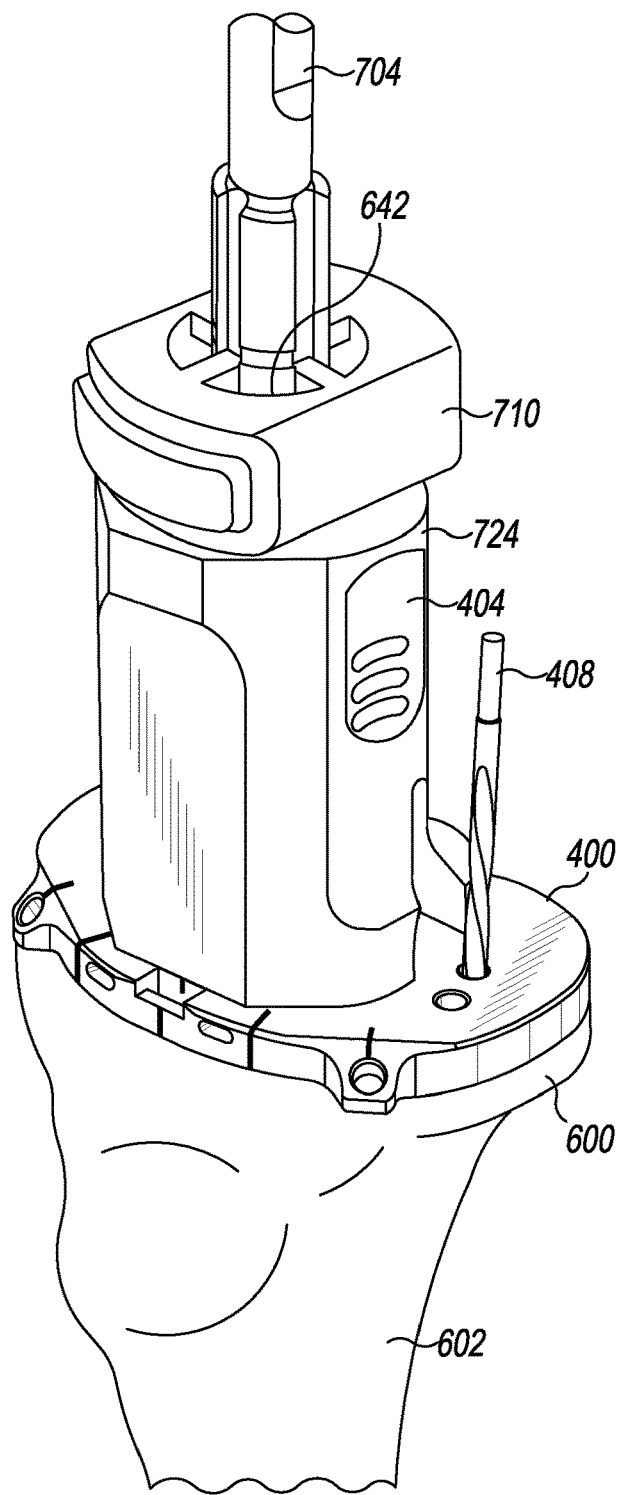
Figure 22:
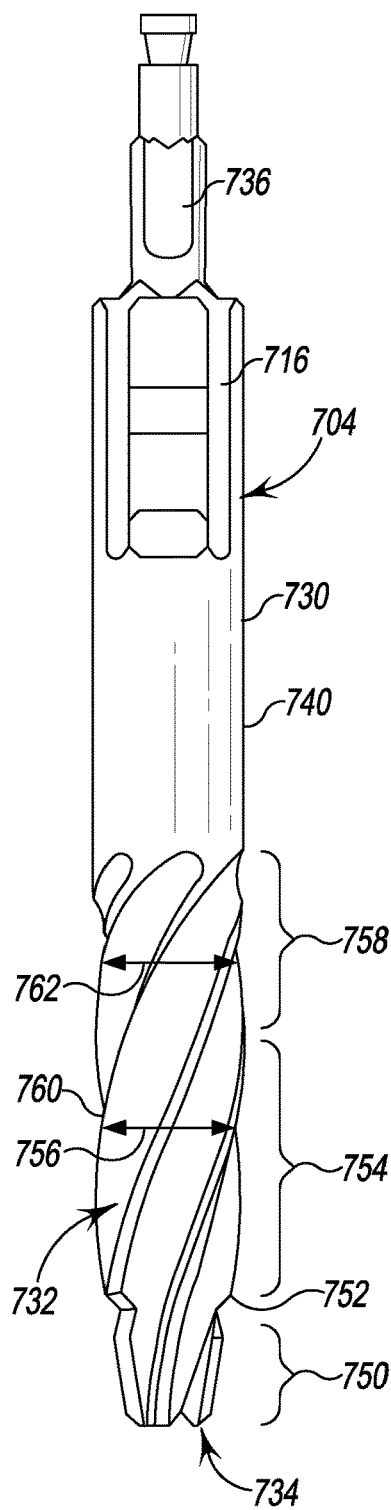
FIG. 22 is a perspective view of another surgical reamer.

Referring now to FIGS. 20-22, the surgeon may utilize another reamer 704 with the tower 404. The system 10 also includes a moveable depth stop 710, which be attached to any of the reamers at an annular slot 642 corresponding to a desired depth. In the illustrative embodiment, the depth stop 710 has a central opening 712 and a plurality of alignment tabs 714 extending inwardly into the opening 712. The central opening 712 has a diameter corresponding to the largest diameter reamer in the system 10. Each reamer, including the reamer 704, includes a plurality of longitudinal slots 716 corresponding in number to the number of alignment tabs 714 of the depth stop 710. As shown in FIG. 20, the bottom surfaces of the slots 716 of each reamer are positioned and sized to be received in an alignment opening 720 defined by the tips of the tabs 714 so that a single depth stop 710 may be used with any size reamer.

In the illustrative embodiment, the depth stop 710 includes a movable plate 722 having a pin that may be advanced into and out of engagement with the annular slot 642 or other aperture to secure the depth stop at a desired position.

As shown in FIG. 21, when the depth stop 710 is properly positioned at the desired annular slot 642 of the reamer 704, the reamer 704 may be advanced into the central cylindrical passageway of a reaming guide adaptor 724 positioned in the guide tower 404. The reamer 704 may then be advanced along the guide adaptor 724 and into contact with the proximal end 600 of the patient's tibia 602. The surgeon may continue to advance the reamer 704 deeper into the patient's tibia until the depth stop 710 contacts the guide adapter 724, thereby reshaping the canal 608 as desired. It should also be appreciated that in some embodiments the reamer and the depth stop 710 may be used with the guide tower alone.

Figure 22A:
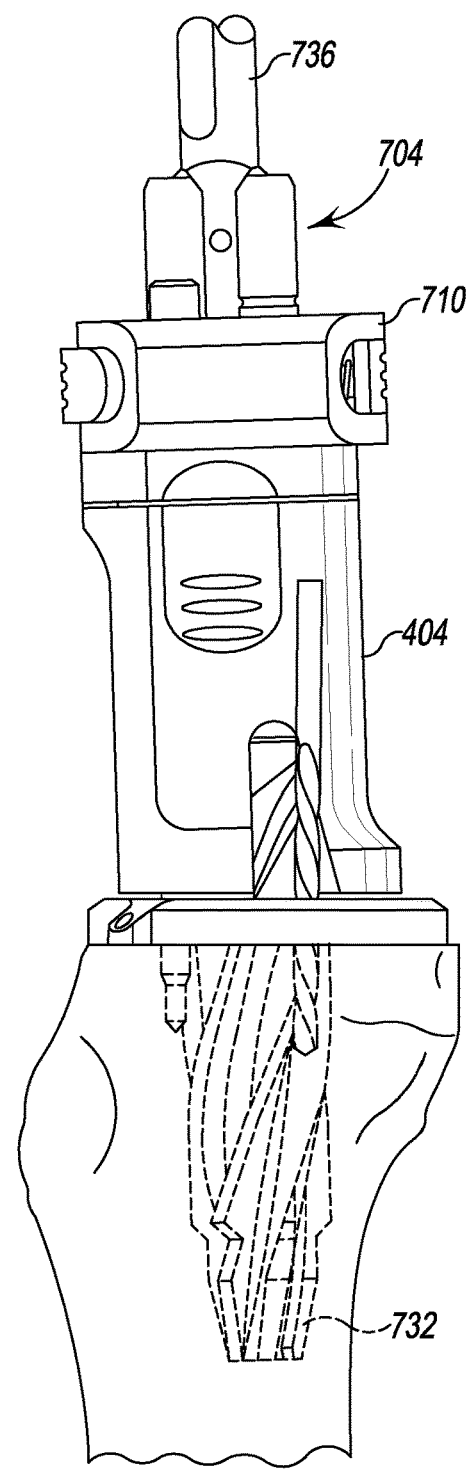

Returning to FIGS. 22-22A, the reamer 704 is shown with the guide tower 404. Similar to the reamer 216, the reamer 704 includes an elongated shaft 730 having a plurality of cutting flutes 732 formed at a distal end 734. A tool shank 736 is formed at the opposite end and is sized to be secured to a surgical drill or other rotary surgical instrument. The elongated shaft 730 includes an outer surface 740 that extends from the cutting flutes 732 to the tool shank 736, and the plurality of longitudinal slots 716 are defined in the outer surface 740.

As shown in FIG. 22, the plurality of cutting flutes 732 include a frustoconical distal section 750 that extends from the distal end 734. The distal section 750 is connected at an edge 752 to a cylindrical middle section 754 of the cutting flutes 732 (i.e., the edges of cutting flutes 732 define a cylindrical shape). The middle section 754 has a diameter 756. The middle section 754 is connected to a proximal section 758 via a tapered section 760. In the illustrative embodiment, the proximal section 758 has a diameter 762 that is greater than the diameter 756 of the middle section 754. The combination of the cylindrical middle section 754, tapered section 760, and proximal section 758 of the cutting flutes 732 cooperate to define an opening a patient's tibia shaped to match the offset adaptor 90 of the prosthetic tibial component 22, as indicated in broken line in FIG. 22A.

Figure 23:
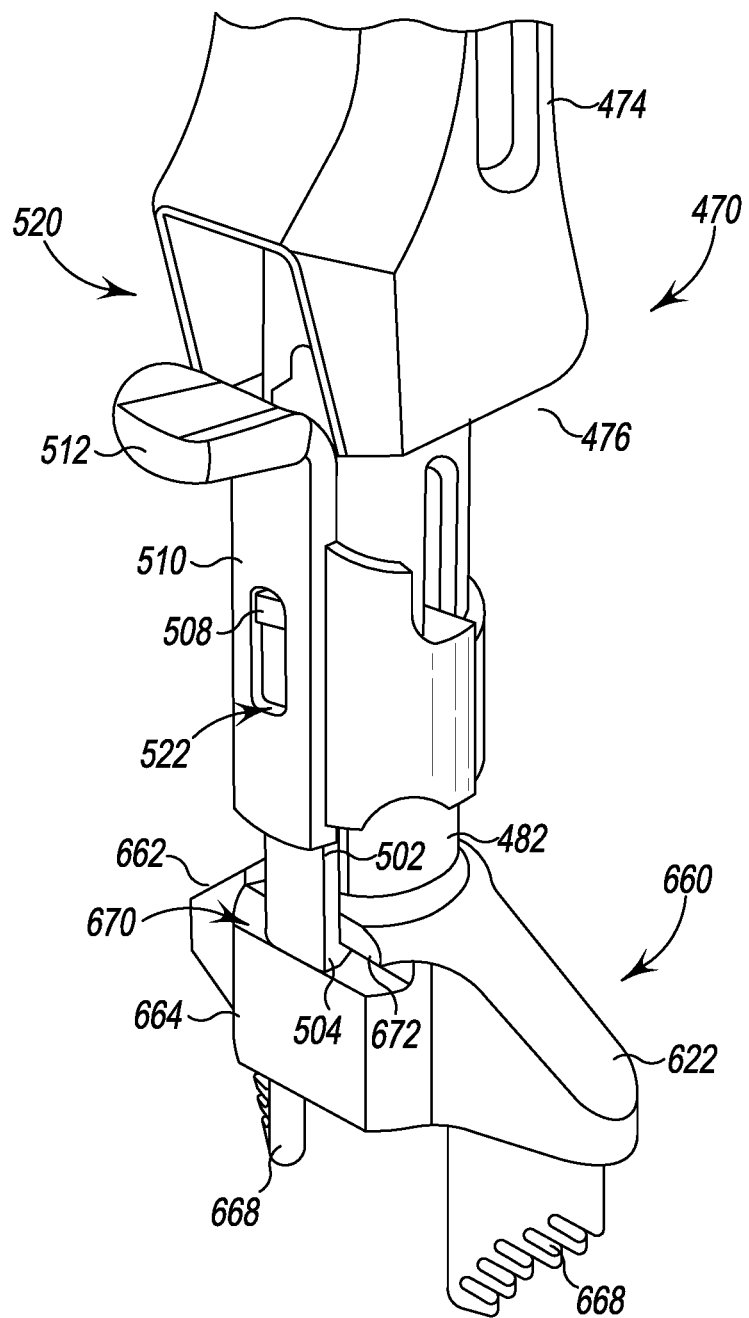

Referring now to FIG. 23, the surgeon may select a keel punch 660 to resize the canal 608 to receive a portion of the elongated stem post 60 of the tibial tray 24. The keel punch 660 includes a pair of arms 662 extending outwardly from a central body 664. Each of the arms 662 includes a number of downwardly-extending cutting teeth 668 the patient's bone to create a passageway for the elongated stem post 60. The central body 664 includes an undercut 670 sized to receive the flange 504 of the lever arm 502 of the impaction handle 470. The central body 664 also includes an engagement plate 672 positioned above the undercut 670, which is configured to engage the locking flange 504, as shown in FIG. 23.

To secure the keel punch 660 the impaction handle 470, a user may press on the flange 512 to cause the bracket 510 of the handle 470 to advance distally toward the strike plate 472. As the bracket 510 advances distally, the flange 512 is advanced into a channel 520 defined in the end 476 of the elongated body 474. Additionally, the proximal edge 522 of the slide plate 514 is advanced into engagement with the tab 508, thereby causing the lever arm 502 to pivot about its axis and moving the locking flange 504 away from the proximal tip 484. The keel punch 660 may then be advanced over the proximal tip 484 and into contact with the cylindrical body section 482, as shown in FIG. 23. The user may then release the flange 512 and a biasing element 530 of the handle 470 urges the bracket 510 proximally, thereby moving the locking flange 504 toward the proximal tip 484 and into engagement with the engagement plate 672 to secure the keel punch 660 to the handle 470.

Figure 24:
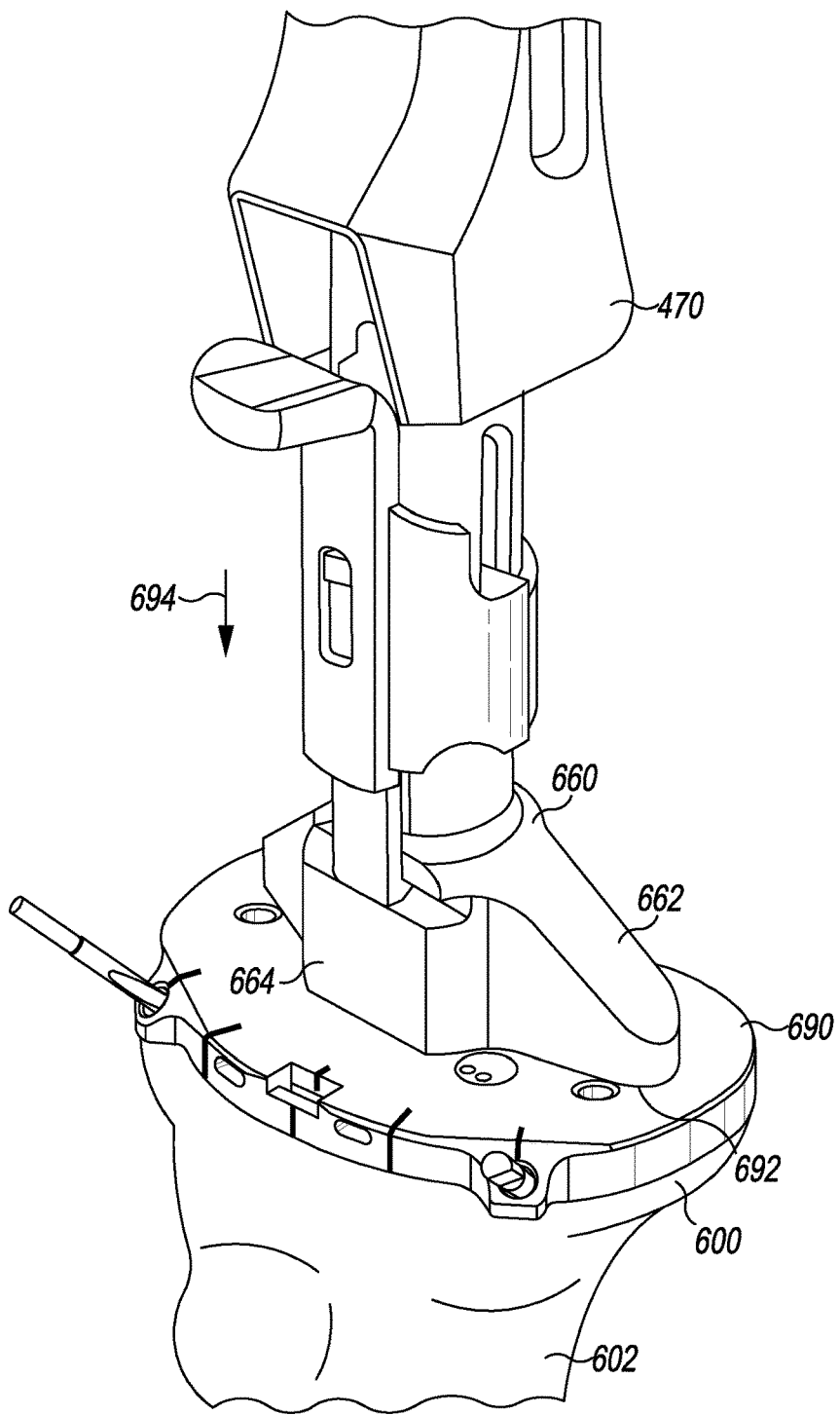

As shown in FIG. 24, the surgeon may remove the tibial plate 400 from the proximal end 600 of the patient's tibia 602 and replace it with another tibial plate 690 including openings 692 sized to receive the arms 662 of the keel punch 660. The surgeon may then advance the impaction handle 470 and keel punch 660 toward the tibial plate 690, as indicated by arrow 694. As the keel punch 660 passes through the tibial plate 690, the cutting teeth 668 engage the patient's bone and reshape the canal to receive the elongated post 60 of the tibial prosthetic component 22.

While the foregoing exemplary embodiments have been described to have a separable tibial tray and a tibial tray insert, it is to be understood that the tibial tray may include condyle receiver bearing surfaces that obviate the need for a separate tibial tray insert.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:

1. An orthopaedic surgical instrument system comprising:
   a surgical reamer including an elongated shaft and a plurality of cutting flutes defined at a distal end of the elongated shaft,
   an attachment base comprising:
      a housing including a main body, an elongated bore that is sized to receive the elongated shaft of the reamer and extends along a longitudinal axis of the main body, and a rail extending from a fixed end on the main body orthogonal to the longitudinal axis to a free end, and
      a locking knob secured to the housing and having a longitudinal bore aligned with the elongated bore of the housing that is sized to receive the elongated shaft of the reamer, the locking knob being rotatable between a first position in which the attachment base is permitted to slide along the elongated shaft of the surgical reamer and a second position in which the attachment base is locked into position on the elongated shaft of the surgical reamer,
   a mounting frame positioned on the rail, the mounting frame being configured to slide relative to the housing along the rail, and
   a cutting block removably coupled to the mounting frame, wherein the locking knob is operable to advance a section of the housing into engagement with the reamer when rotated to the second position, wherein the section of the housing is fixedly attached to the main body of the housing.

2. The orthopaedic surgical instrument system of claim 1, wherein the housing of the attachment base includes a retaining flange configured to engage an inner rib of the locking knob to secure the locking knob to the housing.

3. The orthopaedic surgical instrument system of claim 2, wherein:
   the housing of the attachment base includes an upper shaft extending outwardly from the main body along the longitudinal axis, the upper shaft including a plurality of outer threads and the retaining flange, and
   the locking knob includes a plurality of inner threads configured to engage the plurality of outer threads of the upper shaft.

4. The orthopaedic surgical instrument system of claim 3, wherein the locking knob is moveable along the longitudinal axis between an engaged position in which the plurality of inner threads are engaged with the plurality of outer threads of the upper shaft and a disengaged position in which the plurality of inner threads are spaced apart from the plurality of outer threads of the upper shaft.

5. The orthopaedic surgical instrument system of claim 3, wherein:
   the upper shaft includes a plurality of beams that extend along the longitudinal axis, each beam being spaced apart from an adjacent beam by an elongated slot, and
   the retaining flange includes a plurality of retaining flanges, each retaining flange extending from a tip of each beam.

6. The orthopaedic surgical instrument system of claim 5, wherein:
   each beam has a ramped upper surface, and
   the locking knob includes an annular rib having a conical lower surface that is configured to engage the ramped upper surface of each beam to advance the beams into engagement with the elongated shaft of the surgical reamer.

7. The orthopaedic surgical instrument system of claim 1, wherein the mounting frame includes a locking mechanism that is operable to selectively secure the mounting frame in a position along the rail.

8. The orthopaedic surgical instrument system of claim 7, wherein the mounting frame includes a second locking mechanism that is operable to removeably couple the cutting block to the mounting frame.

9. The orthopaedic surgical instrument system of claim 1, wherein:
   the rail includes a planar outer surface, and
   the mounting frame includes a planar inner surface that corresponds to and engages the planar outer surface of the rail to prevent the mounting frame from rotating about the rail.

10. The orthopaedic surgical instrument system of claim 1, wherein the cutting block includes a plurality of cutting guides sized for insertion of a cutting tool during resection of the patient's tibia.

11. The orthopaedic surgical instrument system of claim 1, further comprising an alignment guide plate sized to be received in one of a plurality of cutting guides of the cutting block to assess a resection of the patient's tibia.

* * * * *